United States Patent
Schings et al.

(10) Patent No.: US 11,937,812 B2
(45) Date of Patent: Mar. 26, 2024

(54) LOCKOUT FEATURE FOR LINEAR SURGICAL STAPLER CARTRIDGE

(71) Applicant: Cilag GmbH International, Zug (CH)

(72) Inventors: Brian D. Schings, Maineville, OH (US); David K. Norvell, Monroe, OH (US)

(73) Assignee: Cilag GmbH International, Zug (CH)

( * ) Notice: Subject to any disclaimer, the term of this patent is extended or adjusted under 35 U.S.C. 154(b) by 0 days.

(21) Appl. No.: 17/489,879

(22) Filed: Sep. 30, 2021

(65) Prior Publication Data

US 2023/0099430 A1    Mar. 30, 2023

(51) Int. Cl.
*A61B 17/072*    (2006.01)
*A61B 17/28*    (2006.01)

(52) U.S. Cl.
CPC .. *A61B 17/072* (2013.01); *A61B 2017/07264* (2013.01); *A61B 2017/07271* (2013.01); *A61B 2017/07285* (2013.01); *A61B 17/2833* (2013.01)

(58) Field of Classification Search
CPC ... A61B 17/072; A61B 17/068; A61B 17/105; A61B 17/1155
See application file for complete search history.

(56) References Cited

U.S. PATENT DOCUMENTS

| | | | |
|---|---|---|---|
| 4,633,861 A * | 1/1987 | Chow | A61B 17/07207 227/19 |
| 5,065,929 A * | 11/1991 | Schulze | A61B 17/07207 227/19 |
| 5,129,570 A * | 7/1992 | Schulze | B25C 5/1686 227/176.1 |
| 5,292,053 A | 3/1994 | Bilotti et al. | |
| 5,333,773 A | 8/1994 | Main et al. | |
| 5,350,104 A | 9/1994 | Main et al. | |
| 5,417,361 A * | 5/1995 | Williamson, IV | A61B 17/07207 227/176.1 |
| 5,533,661 A | 7/1996 | Main et al. | |
| 5,878,938 A | 3/1999 | Bittner et al. | |

(Continued)

FOREIGN PATENT DOCUMENTS

CN    101797174 A    8/2010

OTHER PUBLICATIONS

International Search Report and Written Opinion dated Dec. 22, 2022 for Application No. PCT/IB2022/059165, 11 pgs.

*Primary Examiner* — Nathaniel C Chukwurah
(74) *Attorney, Agent, or Firm* — Frost Brown Todd LLP

(57) ABSTRACT

A staple cartridge assembly capable of coupling with a cartridge channel of a surgical stapler. The staple cartridge includes a staple cartridge body, a swing gate pivotably coupled with the staple cartridge body, and a bridge member extending across the central slot and located proximally relative to the swing gate. The staple cartridge body defines a central slot dimensioned to slidably receive a firing beam of the surgical stapler. The staple cartridge body includes a proximal end, a distal end, and a staple deck extending between the proximal end and the distal end. The staple deck defines staple openings. The swing gate can pivot between a first position and a second position. The swing gate extends across the central slot in the first position, while the swing gate extends alongside the central slot in the second position. The bridge member defines a closed proximal end of the central slot.

20 Claims, 20 Drawing Sheets

(56) References Cited

U.S. PATENT DOCUMENTS

| | | | |
|---|---|---|---|
| 7,055,730 B2* | 6/2006 | Ehrenfels | A61B 17/07207 227/176.1 |
| 8,910,847 B2 | 12/2014 | Nalagatla et al. | |
| 9,155,537 B2* | 10/2015 | Katre | A61B 17/07207 |
| 9,713,469 B2 | 7/2017 | Leimbach et al. | |
| 9,907,552 B2 | 3/2018 | Measamer et al. | |
| 9,936,949 B2 | 4/2018 | Measamer et al. | |
| 10,631,866 B2 | 4/2020 | Laurent et al. | |
| 10,667,818 B2 | 6/2020 | McClain et al. | |
| 10,687,819 B2 | 6/2020 | Stokes et al. | |
| 10,709,452 B2 | 7/2020 | DiNardo et al. | |
| 10,874,398 B2 | 12/2020 | Baxter, III et al. | |
| 10,898,187 B2 | 1/2021 | Deck et al. | |
| 10,905,419 B2 | 2/2021 | Schings et al. | |
| 10,932,781 B2 | 3/2021 | Jones et al. | |
| 11,033,266 B2 | 6/2021 | Jones et al. | |
| 11,045,193 B2 | 6/2021 | Schings et al. | |
| 2009/0308907 A1 | 12/2009 | Nalagatla et al. | |
| 2015/0083772 A1 | 3/2015 | Miller et al. | |
| 2018/0132849 A1 | 5/2018 | Miller et al. | |
| 2018/0168625 A1 | 6/2018 | Posada et al. | |
| 2019/0239882 A1 | 8/2019 | Mclain et al. | |
| 2020/0046353 A1 | 2/2020 | Deck et al. | |
| 2021/0038223 A1 | 2/2021 | Schings et al. | |

* cited by examiner

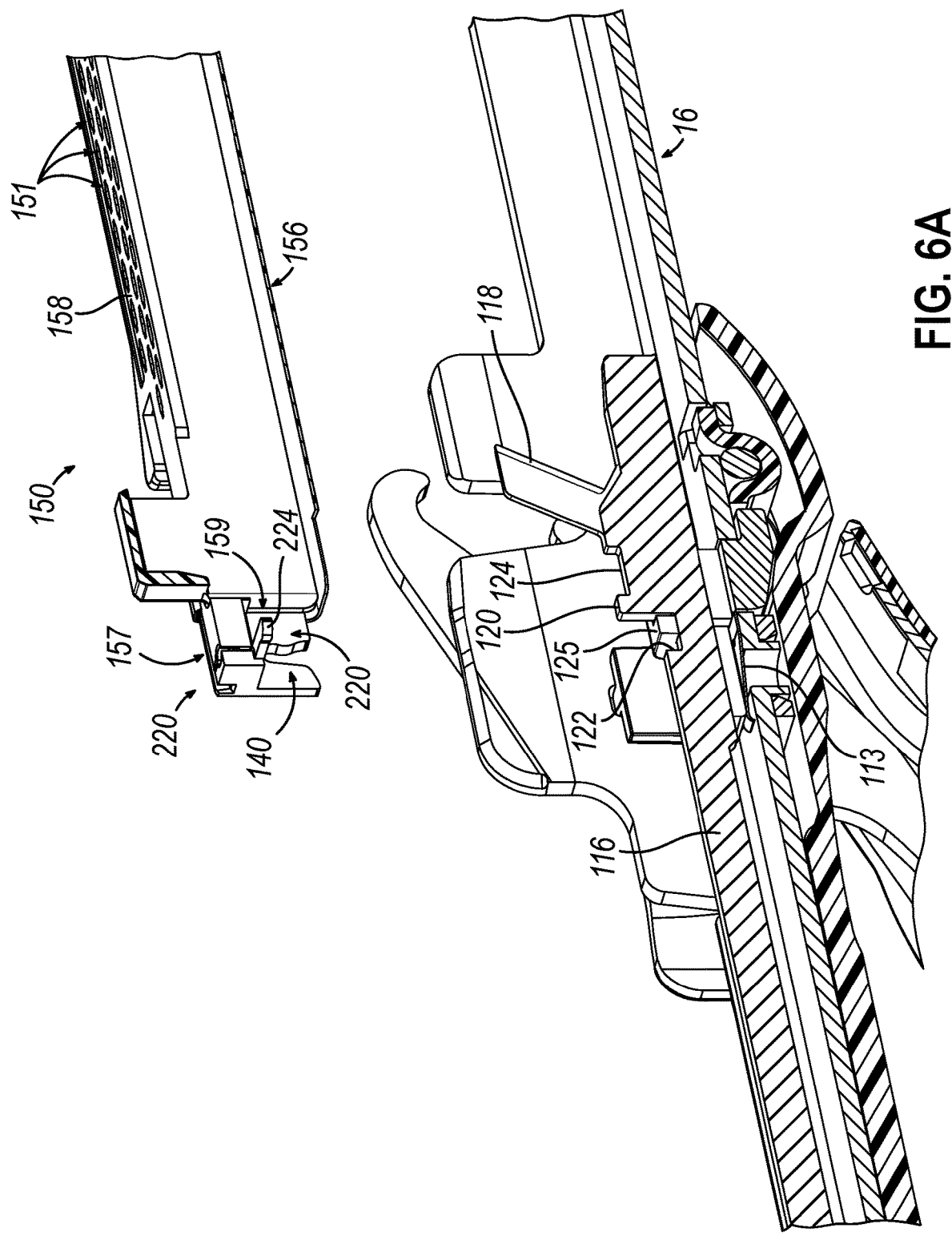

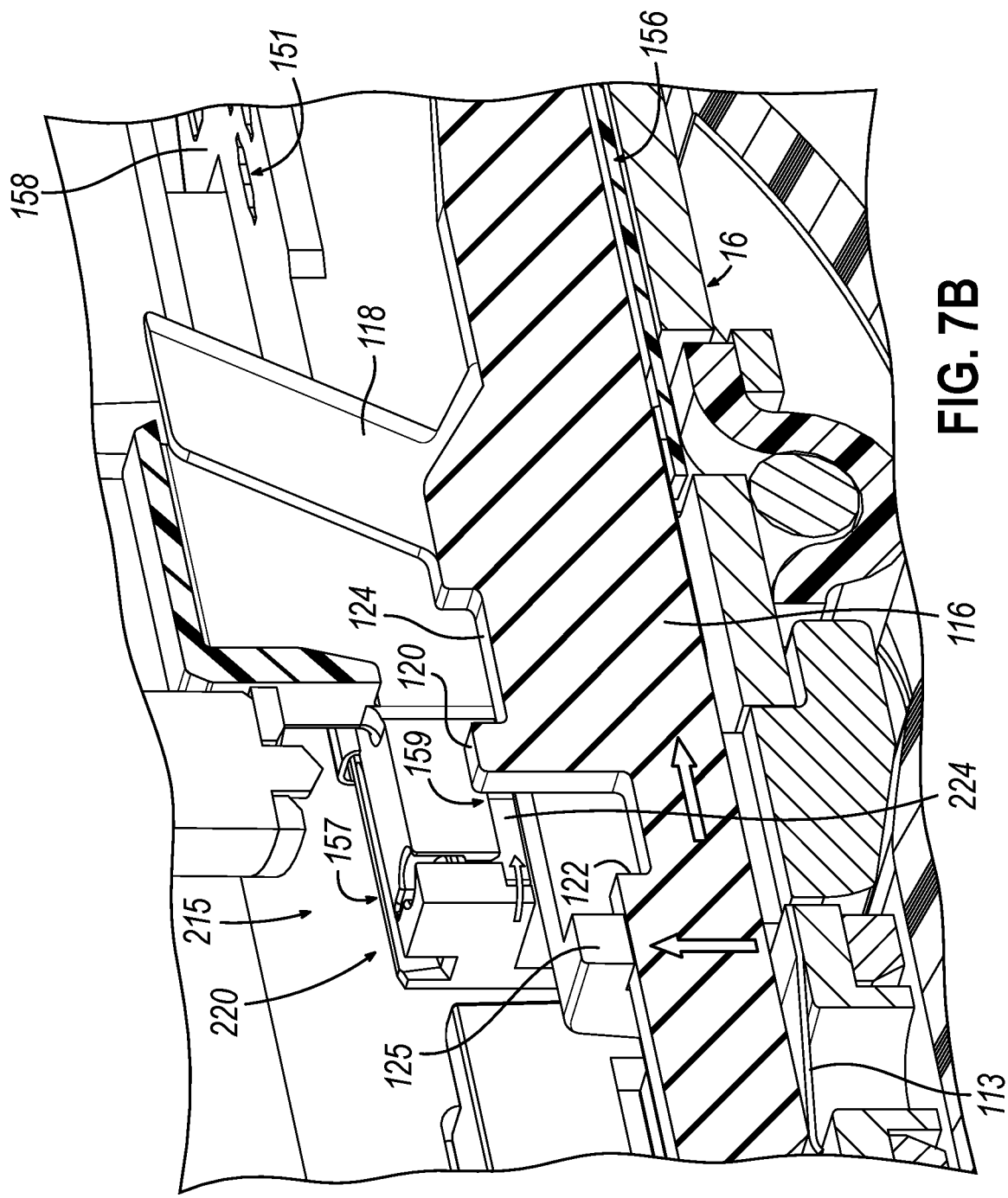

LOCKOUT FEATURE FOR LINEAR SURGICAL STAPLER CARTRIDGE

BACKGROUND

In some surgical operations, such as a gastrointestinal anastomosis, it may be desirable to clamp down on one or more layers of tissue, cut through the clamped layers, and simultaneously drive staples through the layers to substantially seal the severed layers of tissue together near their severed ends. One such instrument that may be used in such operations is a linear surgical stapler, also referred to as a "linear cutter." A linear surgical stapler generally includes a first half (referred to as a "cartridge half" or "reload half") having a distal jaw configured to support a staple cartridge (or "reload"), and a second half (referred to as an "anvil half") having a distal jaw that supports an anvil surface having staple forming features. The stapler further includes a moveable clamp lever configured to releasably clamp the stapler halves together. The stapler halves are configured to pivot relative to one another to receive and clamp tissue between the two distal jaws when the clamp lever is closed. A firing assembly of the stapler is configured to be actuated to cut the clamped layers and simultaneously drive staples through the tissue on either side of the cut line. After firing the stapler, the clamp lever may be opened, and the stapler halves separated to release the severed and stapled tissue.

While various kinds of surgical stapling instruments and associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

FIG. 6A depicts a sectional perspective view of the staple cartridge assembly of FIG. 4 aligned for coupling with the cartridge half of FIG. 1, taken along line 4-4 of FIG. 2, where the firing assembly of FIG. 3 is in a locked-out configuration;

FIG. 7B depicts a sectional perspective view of the cartridge half and the anvil half of FIG. 1 in the fully closed position, taken along line 4-4 of FIG. 2, where the firing assembly of FIG. 3 is in an unlocked configured and a partially fired position;

Figure 1:
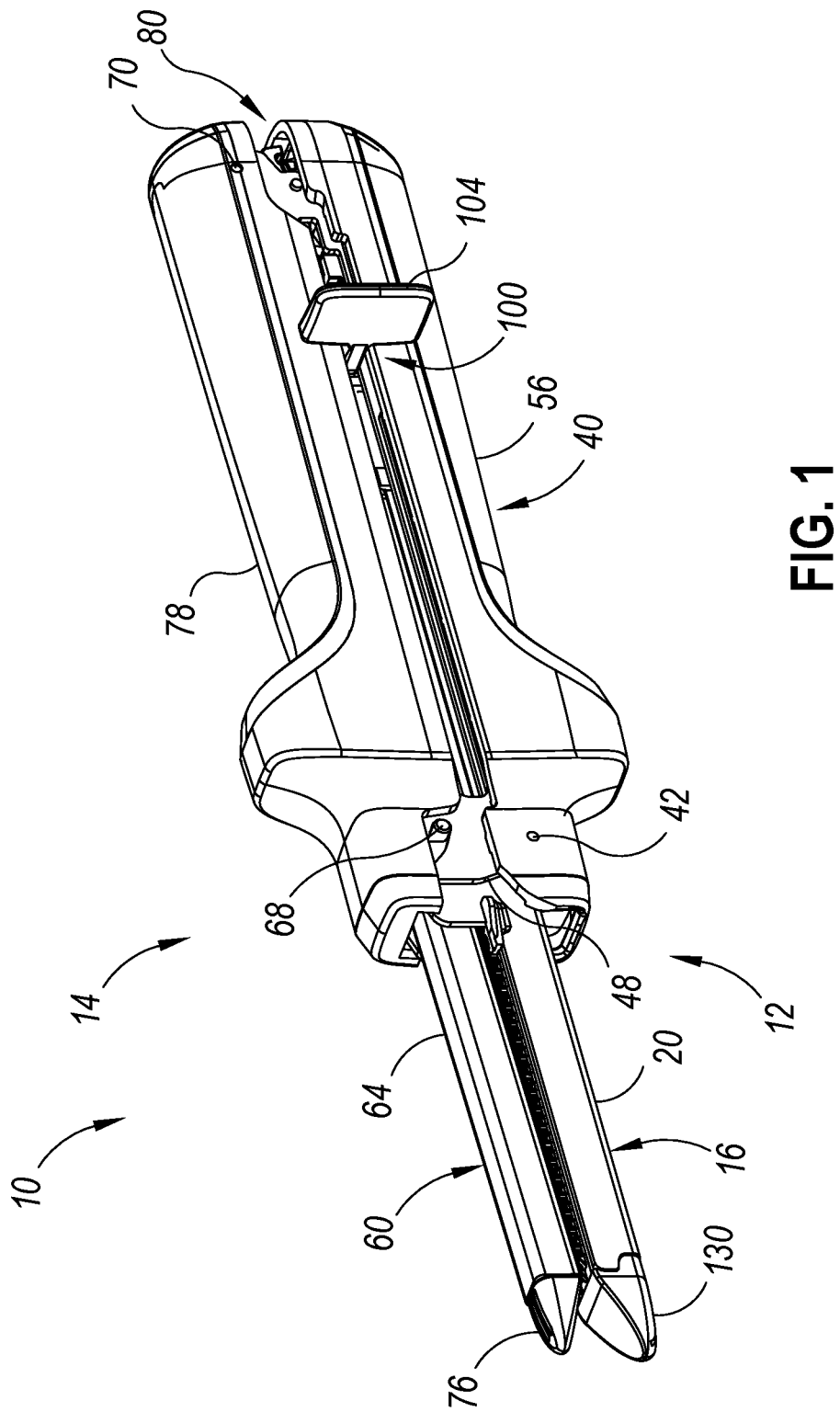
FIG. 1 depicts a perspective view of an exemplary linear surgical stapler, showing a cartridge half and an anvil half of the stapler coupled together with a clamp lever of the cartridge half in a fully closed position.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

For clarity of disclosure, the terms "proximal" and "distal" are defined herein relative to a surgeon, or other operator, grasping a surgical instrument having a distal surgical end effector. The term "proximal" refers to the position of an element arranged closer to the surgeon, and the term "distal" refers to the position of an element arranged closer to the surgical end effector of the surgical instrument and further away from the surgeon. Moreover, to the extent that spatial terms such as "upper," "lower," "vertical," "horizontal," or the like are used herein with reference to the drawings, it will be appreciated that such terms are used for exemplary description purposes only and are not intended to be limiting or absolute. In that regard, it will be understood that surgical instruments such as those disclosed herein may be used in a variety of orientations and positions not limited to those shown and described herein.

As used herein, the terms "about" and "approximately" for any numerical values or ranges indicate a suitable dimensional tolerance that allows the part or collection of components to function for its intended purpose as described herein.

I. Exemplary Linear Surgical Stapler

A. Overview of Linear Surgical Stapler

Figure 2:
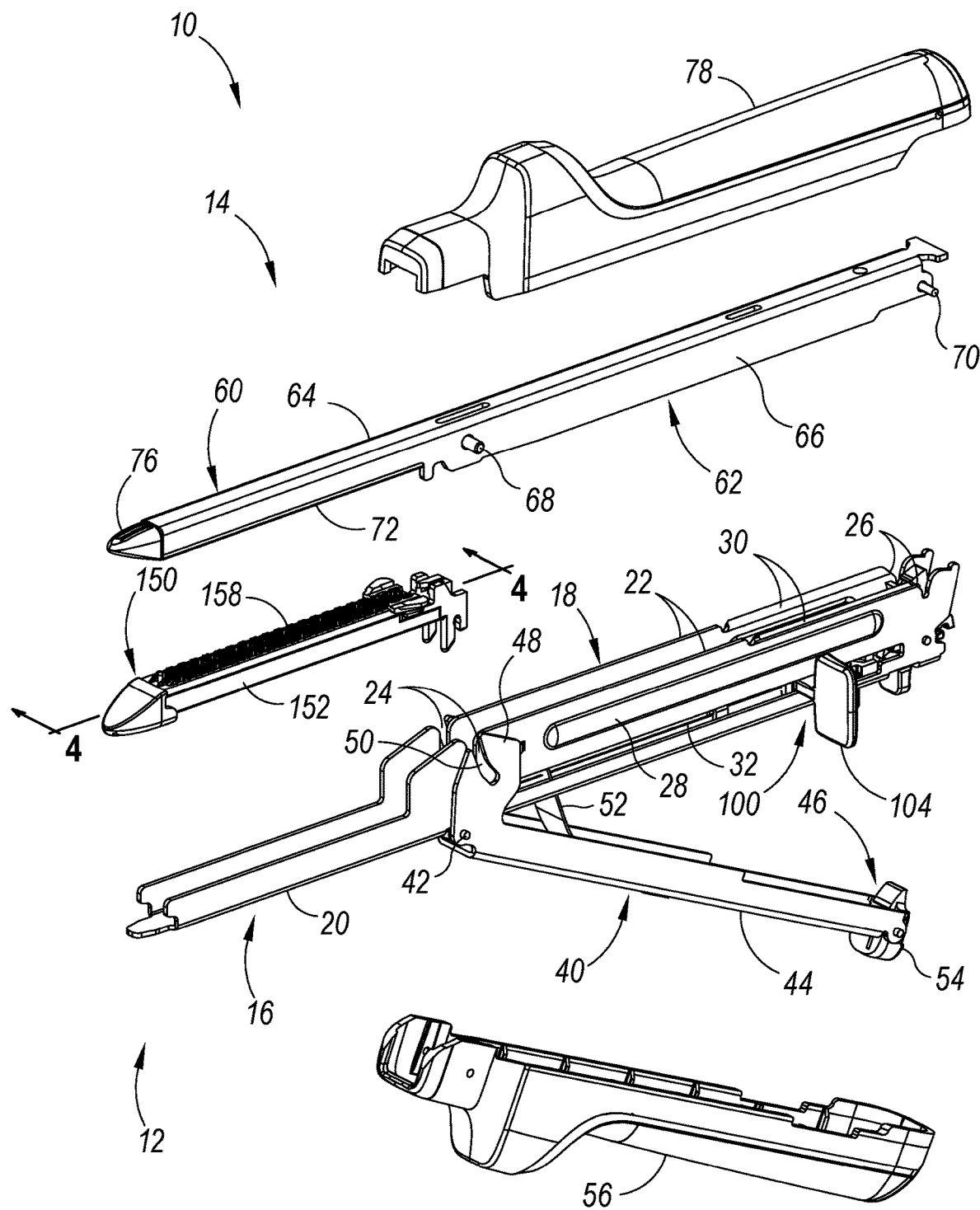
FIG. 2 depicts an exploded perspective view of the linear surgical stapler of FIG. 1.

FIGS. 1-2 show an exemplary linear surgical stapler (10) (also referred to as a "linear cutter") suitable for use in a variety of cutting and stapling procedures, such as a gastrointestinal anastomosis procedure. Linear surgical stapler (10) includes a cartridge half (12) (also referred to as a "reload half") and an anvil half (14) configured to releasably couple together to clamp tissue therebetween for simultaneous cutting and stapling of the clamped tissue.

Cartridge half (12) includes an elongate cartridge channel (16) having a proximal frame portion (18) and a distal jaw portion (20). Proximal frame portion (18) slidably retains a firing assembly (100) and includes a laterally opposed pair of upright side flanges (22). While in the current example, firing assembly (100) is associated with cartridge half (12), it should be understood that in some examples, firing assembly (100) may be associated with anvil half (14). Each side flange (22) includes a vertical slot (24) arranged at a distal end thereof, and a tapered notch (26) arranged at a proximal end thereof. An outwardly projecting stiffening rib (28) extends longitudinally between the distal slot (24) and proximal notch (26) of each side flange (22) and is configured to provide the side flange (22) with enhanced stiffness. An outwardly flared upper segment (30) defines an upper edge of a proximal portion of each side flange (22) and is configured to facilitate receipt of anvil half (14) by cartridge half (12). Each side flange (22) further includes an elongate firing slot (32) extending longitudinally between proximal notch (26) and distal slot (24) along a lower side of side flange (22). Elongate firing slots (32) are configured to guide firing assembly (100) between proximal and distal positions. Firing assembly (100) is described in greater detail below in connection with FIG. 3. Distal jaw portion (20) of cartridge channel (16) is configured to receive a staple cartridge assembly (150) (or "reload"), which may be configured in accordance with the teachings of U.S. Pat. Pub. 2021/0038223, entitled "Linear Surgical Stapler," published on Feb. 11, 2021, issued as U.S. Pat. No. 11,229,433 on Jan. 25, 2022, the disclosure of which is incorporated by reference herein.

Cartridge half (12) further includes a clamp lever (40) (also referred to as a "latch lever") pivotably coupled to cartridge channel (16) with a clamp lever pivot pin (42), which is arranged in approximate alignment with distal slots (24) of cartridge channel side flanges (22). Clamp lever (40) includes an elongate lever arm (44) having a free proximal end (46) and a distal end that is pivotably coupled to a lower portion of cartridge channel (16) with pivot pin (42). A pair of opposed jaws (48) extend distally from the distal end of lever arm (44) alongside cartridge channel side flanges (22). Each jaw (48) includes a curved slot (50) having a closed proximal end and an open distal end configured to receive a latch pin (68) of anvil half (14), as described below.

Clamp lever (40) is operable to pivot relative to cartridge channel (16) between an open position in which proximal end (46) of lever arm (44) is spaced from cartridge channel frame portion (18), and a closed position in which proximal end (46) confronts cartridge channel frame portion (18). Actuation of clamp lever (40) from the open position to the closed position operates to capture the opposed lateral ends of latch pin (68) within clamp lever jaw slots (50), and thereby clamp anvil half (14) against cartridge half (12). In that regard, the curvature of each jaw slot (50) defines respective upper and lower camming surfaces configured to engage and draw the respective lateral end of latch pin (68) toward cartridge channel (16) as clamp lever (40) is pivotably closed. A resilient member shown in the form of a flat spring (52) biases lever arm (44) toward the open position. Accordingly, flat spring (52) promotes disengagement of clamp lever jaws (48) from anvil half latch pin (68) upon initial advancement of clamp lever (40) from the closed position toward the open position. As best shown in FIG. 2, clamp lever (40) further includes a latch member (54) arranged at proximal end (46) of lever arm (44). Clamp lever latch member (54) is configured to resiliently and releasably engage a proximal end of cartridge channel frame portion (18) and thereby releasably retain clamp lever (40) in the closed position, for instance while stapler (10) is being fired.

Anvil half (14) of linear surgical stapler (10) includes an elongate anvil channel (60) having a proximal frame portion (62) and a distal jaw portion (64). Proximal frame portion (62) includes a laterally opposed pair of upright side flanges (66) that are configured to be received between cartridge channel side flanges (22) when anvil half (14) is coupled with cartridge half (12). A distal latch projection in the form of latch pin (68) extends laterally through the distal ends of anvil channel side flanges (66), and a proximal pivot projection in the form of a proximal pin (70) extends laterally through the proximal ends of anvil channel side flanges (66). Anvil pins (68, 70) are configured to facilitate coupling of anvil half (14) with cartridge half (12).

Distal jaw portion (64) of anvil half (14) supports an anvil plate (72) that defines an anvil surface having a plurality of staple forming pockets (not shown) configured to deform legs of staples ejected by staple cartridge assembly (150) when stapler (10) is fired, for example as described in greater detail in U.S. Pat. Pub. 2021/0038223, issued as U.S. Pat. No. 11,229,433 on Jan. 25, 2022, incorporated by reference above. In some versions, the anvil surface may be formed integrally with distal jaw portion (64). Distal jaw portion (64) of anvil half (14) additionally supports a tapered distal tip member (76).

As shown in FIG. 2, linear surgical stapler (10) further includes a plurality of shrouds (56, 78) that cover select portions of stapler (10) and promote effective grip and manipulation of stapler (10) by an operator during use. In the present example, a clamp lever shroud (56) is affixed to and covers an outwardly facing side of clamp lever (40) such that clamp lever shroud (56) is configured to pivot with clamp lever (40) relative to cartridge channel (16). Additionally, an anvil shroud (78) is affixed to and covers an outwardly facing side of anvil channel (60).

Figure 3:
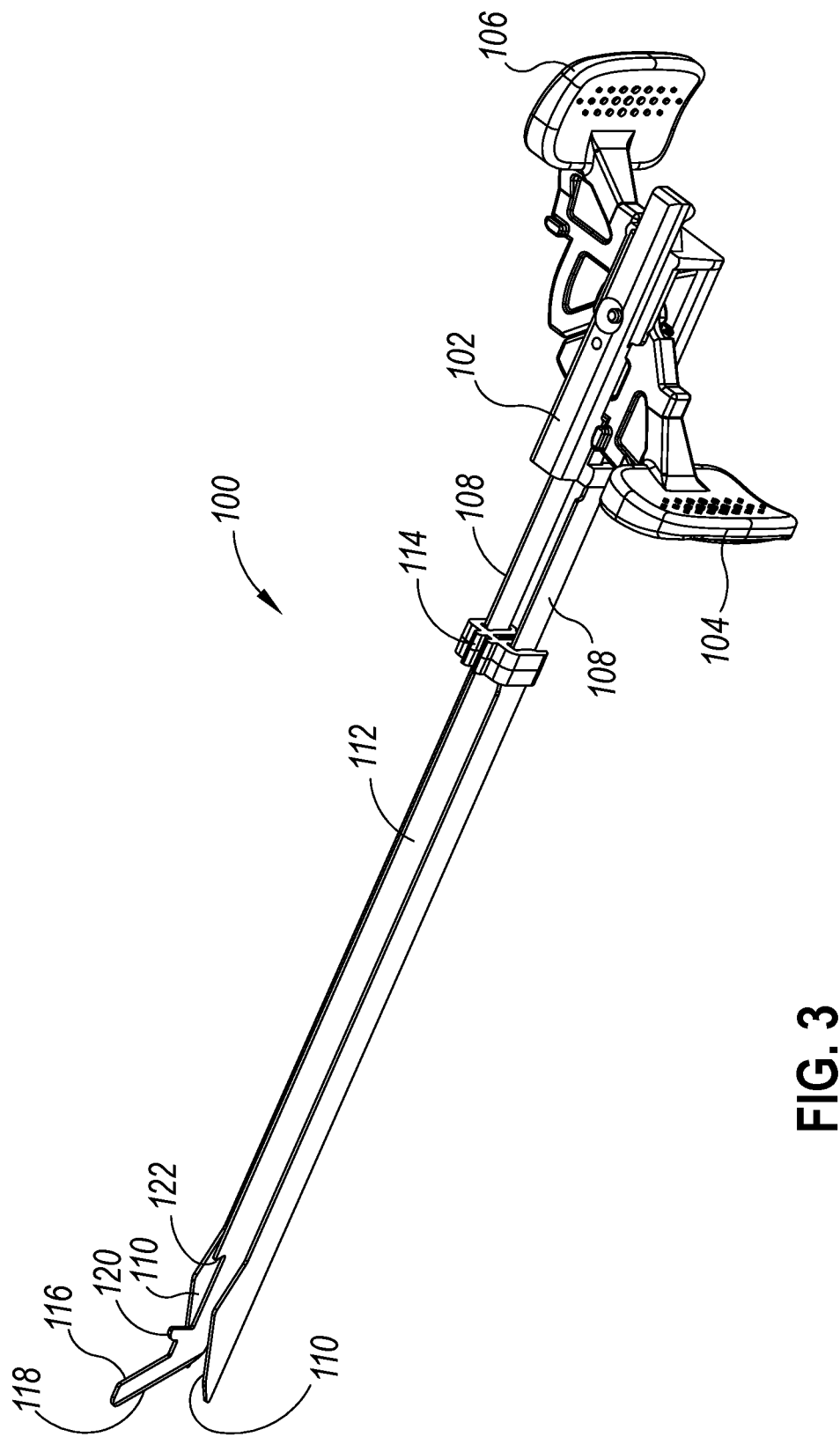
FIG. 3 depicts a top perspective view of a firing assembly of the linear surgical stapler of FIG. 1.

As shown best in FIG. 3, firing assembly (100) of cartridge half (12) includes a slide block (102), a pair of actuators (104, 106) (or "firing knobs") pivotably coupled to slide block (102), and a plurality of elongate beams (108, 112) extending distally from slide block (102). A pair of side beams (108) are coupled at their proximal ends to a distal end of slide block (102) and terminate distally in a pair of cam ramps (110). Cam ramps (110) are configured to engage the undersides of staple drivers (not shown) housed within staple cartridge assembly (150) and actuate staple drivers upwardly to thereby drive (or "fire") staples from cartridge assembly (150) into tissue clamped between staple cartridge assembly (150) and anvil plate (72). A center beam (112) is coupled with side beams (108) via a connecting structure (114) (or "knife block") spaced distally from slide block (102). Center beam (112) terminates distally in a distally angled knife member (116) having a distal cutting edge (118) configured to cut tissue clamped between the distal portions of stapler halves (12, 14). A distal portion of center beam (112) additionally includes a sweep away projection (120) proximal to knife member (116), and a distally facing lockout projection (122) proximal to stop element (120). As will be described in greater detail below, sweep away projection (120) and lockout projection (122) help form a lockout assembly (215) (see FIGS. 6A-7D) configured to (A) lockout firing assembly (100) prior to staple cartridge assembly (150) being suitably loaded into distal jaw portion (20) and (B) lockout firing assembly (100) after firing assembly (100) has been distally advanced and proximally retracted within cartridge assembly (150) to suitably fire staples and sever tissue in accordance with the description herein.

Each actuator (104, 106) of firing assembly (100) is configured and rotatable relative to slide block (102) between a deployed position and a retracted position such that only one actuator (104, 106) may be deployed at a time, for example as described in greater detail in U.S. patent application Ser. No. 16/102,164, issued as U.S. Pat. No. 10,898,187 on Jan. 26, 2021, incorporated by reference above. In the deployed position, an actuator (104, 106) may be driven distally by an operator to actuate firing assembly (100) distally through stapler (10) and thereby simultaneously cut and staple tissue clamped between stapler halves (12, 14).

B. Overview of Exemplary Staple Cartridge

FIGS. 2 and 4-6B show exemplary staple cartridge assembly (150). Staple cartridge assembly (150) includes a cartridge body (152) dimensioned to couple with jaw portion (20) of cartridge channel (16) described above. A portion of cartridge body (152) is dimensioned to fit within the confines of cartridge channel (16); while a proximal end of cartridge body (152) defines a pair of coupling cutouts (140) to further promote coupling of cartridge body (152) with jaw portion (20). Coupling cutouts (140) may be dimensioned to receive pin (42). Alternatively, coupling cutouts (140) may be dimensioned to receive any other suitable component of cartridge channel (16) as would be apparent to one skilled in the art in view of the teachings herein. In some instances, the portion of cartridge body (152) defining coupling cutouts (140) may be resilient in order to couple with jaw pin (42) via a snap fitting. Therefore, an exemplary staple cartridge assembly (150) may be coupled with cartridge channel (16), fired in accordance with the description herein, removed from cartridge channel (16), and subsequently replaced with another staple cartridge assembly (150).

Cartridge body (152) includes a deck surface (158) defining a plurality of staple openings (151). Deck surface (158) is configured to face toward anvil plate (72) when cartridge body (152) is suitably coupled within jaw portion (20). Each staple opening (151) houses a respective staple driver (not shown) and staple (not shown). As mentioned above, cam ramps (110) of firing assembly (100) are configured to engage the undersides of staple drivers (not shown) housed within staple cartridge assembly (150) and actuate staple drivers upwardly to thereby drive (or "fire") staples out of staple openings (151) into tissue clamped between staple cartridge assembly (150) and anvil plate (72). Cartridge body (152) also defines a central slot (156) dimensioned to slidably receive knife member (116) of firing assembly (100) such that knife member (116) may actuate through central slot (156) to sever tissue in accordance with the description herein.

Figure 4:
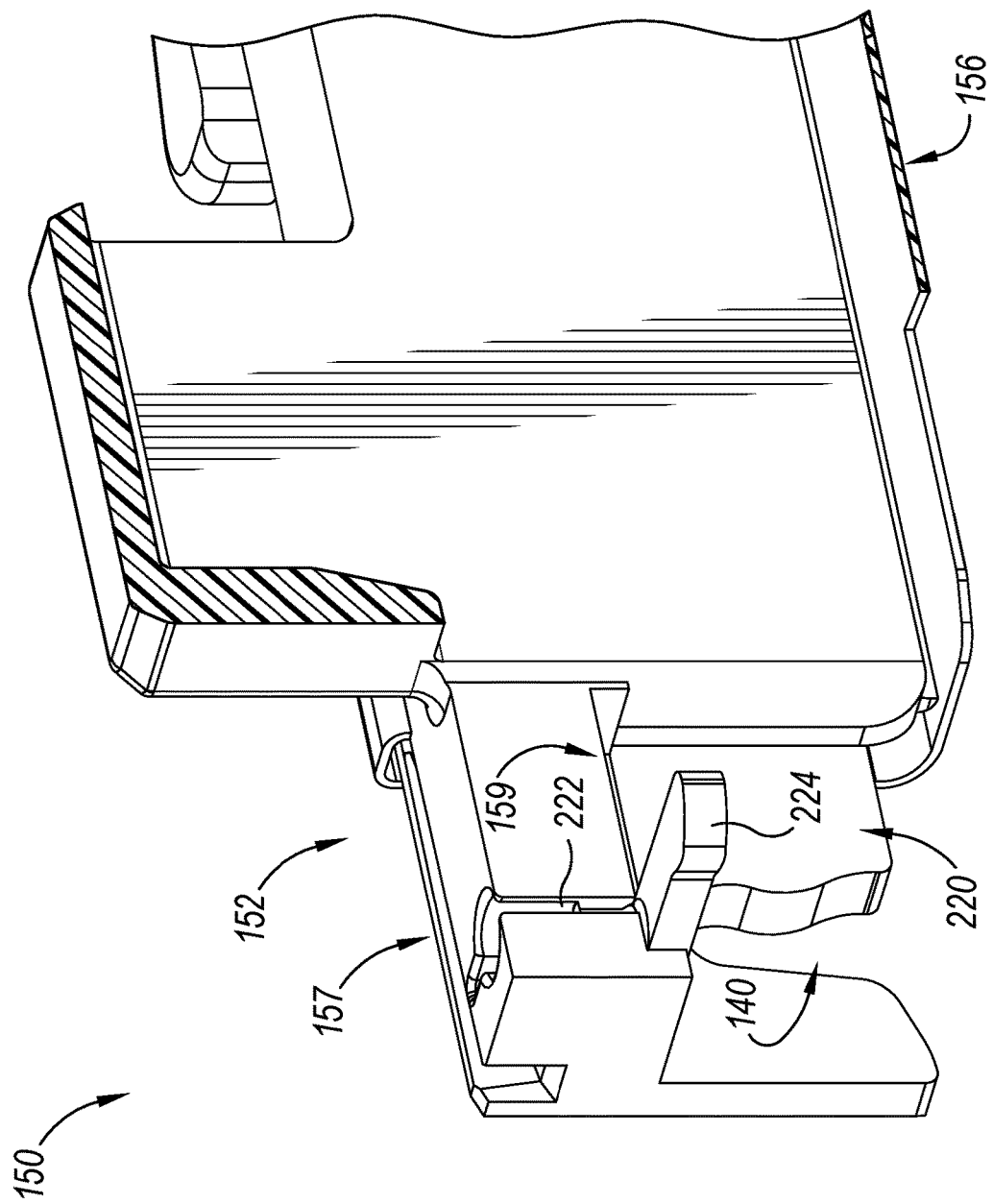
FIG. 4 depicts a sectional perspective view of a staple cartridge assembly, taken along line 4-4 of FIG. 2.
Figure 5:
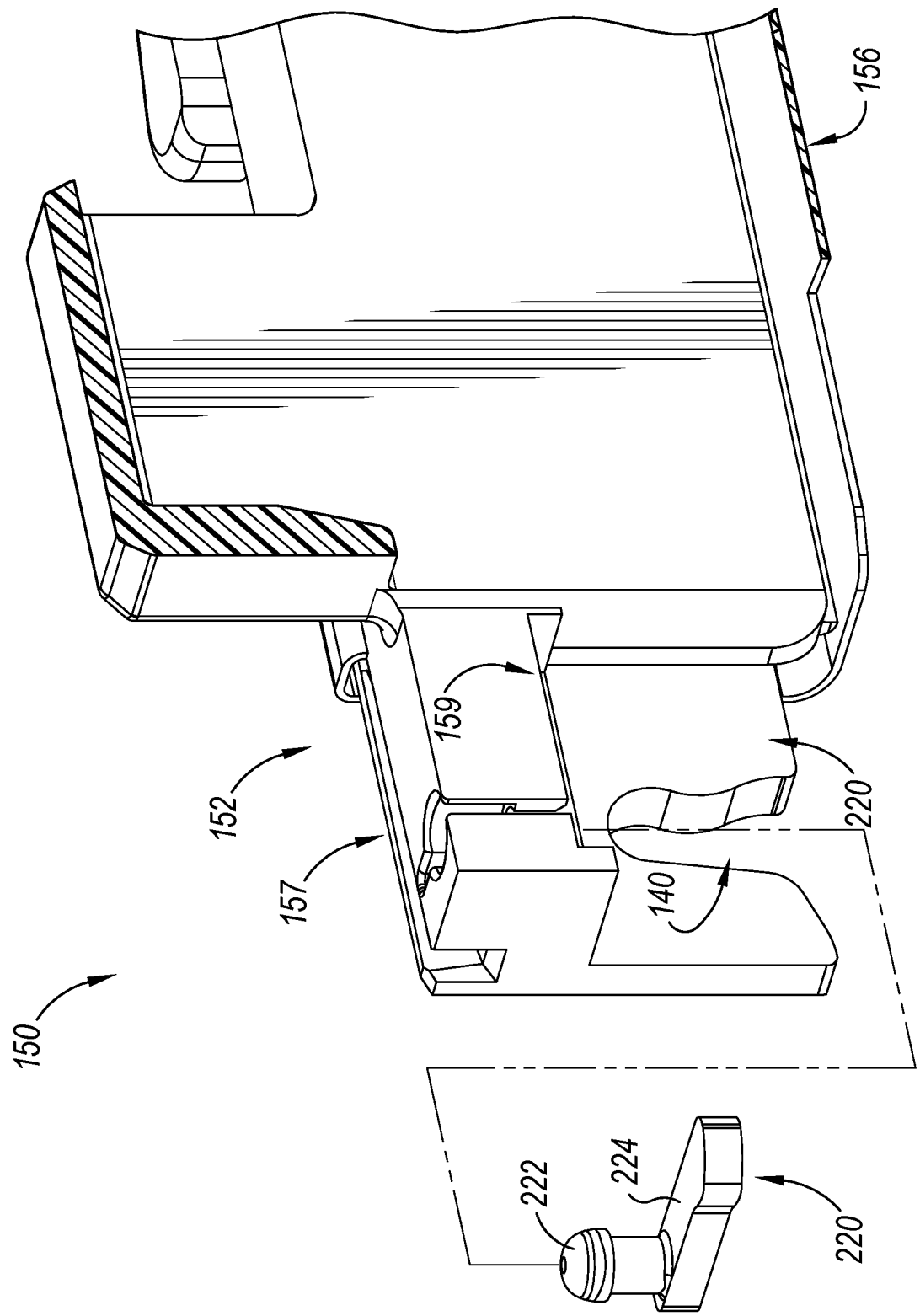
FIG. 5 depicts a sectional exploded view of the staple cartridge assembly of FIG. 4, taken along line 4-4 of FIG. 2.

As shown in FIGS. 4-5, a proximal end of cartridge body (152) defines a pivot bore (157) and a sweep away recess (159). As will be described in greater detail below, pivot bore (157) and sweep away recess (159) are configured to house lockout swing gate (220) of lockout assembly (215).

C. Exemplary Firing of Linear Surgical Stapler

As mentioned above, staple cartridge assembly (150) is configured to couple with distal jaw portion (20) of cartridge channel (16). Additionally, as mentioned above, staple cartridge assembly (150) is configured to slidingly receive select components of firing assembly (100).

In particular, staple cartridge assembly (150) is configured to couple with cartridge channel (16) such that staple deck (158) faces toward anvil plate (72) of anvil channel (60). When staple cartridge assembly (150) is suitably coupled with cartridge channel (16), pin (70) may be inserted into tapered notches (26) to initially pivotally couple cartridge half (12) with anvil half (14). Next, cartridge half (12) and anvil half (14) may be initially pivots via pin (70) and notches (26) such that curved slots (50) of clamp lever (40) may initially receive latch pin (68). With latch pin (68) received within curved slots (50), clamp lever (40) may be further pivoted toward upright side flange (22) to thereby clamp anvil half (14) against cartridge half (12) such that staple deck (158) and anvil plate (72) suitably clamp tissue.

While tissue is suitably clamped, an operator may suitably drive firing assembly (100) by distally grasping either actuator (104, 106) and distally sliding it along the path defined by firing slot (32). Staple cartridge assembly (150) is configured to slidingly receive cam ramps (110) and distal cutting edge (118) of firing assembly (100) such that (A) cam ramps (110) may actuate staple drivers (not shown) upwardly to drive staples through tissue and against anvil plate (72) to staple tissue, and (B) distal cutting edge (118) may acuate through a central slot (156) defined a cartridge body (152) of staple cartridge assembly (150) to simultaneously cut tissue. Therefore, distal actuation of actuator (104, 106) along a respective firing slot (32) simultaneously staples and severs the grasped tissue. Once staple cartridge assembly (150) is suitably fired, the operator may proximally retract actuator (104, 106) along firing slot (32) such that distal cutting edge (118) and cam ramps (110) retract to a pre-fired position.

With actuator (104, 106) suitably retracted, the operator may then pivot clamp lever (40) away from side flanges (22) and pivot cartridge half (12) and anvil half (14) away from each other to release tissue. If desired, the operator may replace the spent cartridge with a new reload, and repeat the process described above.

D. Exemplary Lockout Assembly

FIGS. 6A-7D show an exemplary lockout assembly (215) configured to lockout firing assembly (100) prior to staple cartridge assembly (150) being suitably loaded into cartridge channel (16). Additionally, lockout assembly (215) is configured to lockout firing assembly (100) after cam ramps (110) and knife member (116) have been fired within unspent staple cartridge assembly (150) and then proximally retracted back into the pre-fired position, thus inhibiting subsequent distal actuations of knife member (116) and potentially cutting tissue without also stapling the cut tissue. It will therefore be understood that lockout assembly (215) is configured to function as both an "absent cartridge" lockout as well as a "spent cartridge" lockout.

Lockout assembly (215) includes a lockout swing gate (220) pivotably coupled with a proximal end of cartridge body (152), a lockout block (125) fixed within cartridge channel (16), and a leaf spring (113) within cartridge channel (16). As will be described in greater detail below, leaf spring (113) is configured to bias knife member (116) into engagement with lockout block (125) when knife member (116) is in the proximal position (as seen in FIG. 6A), thereby urging knife member (116) into a locked configuration.

Figure 6B:
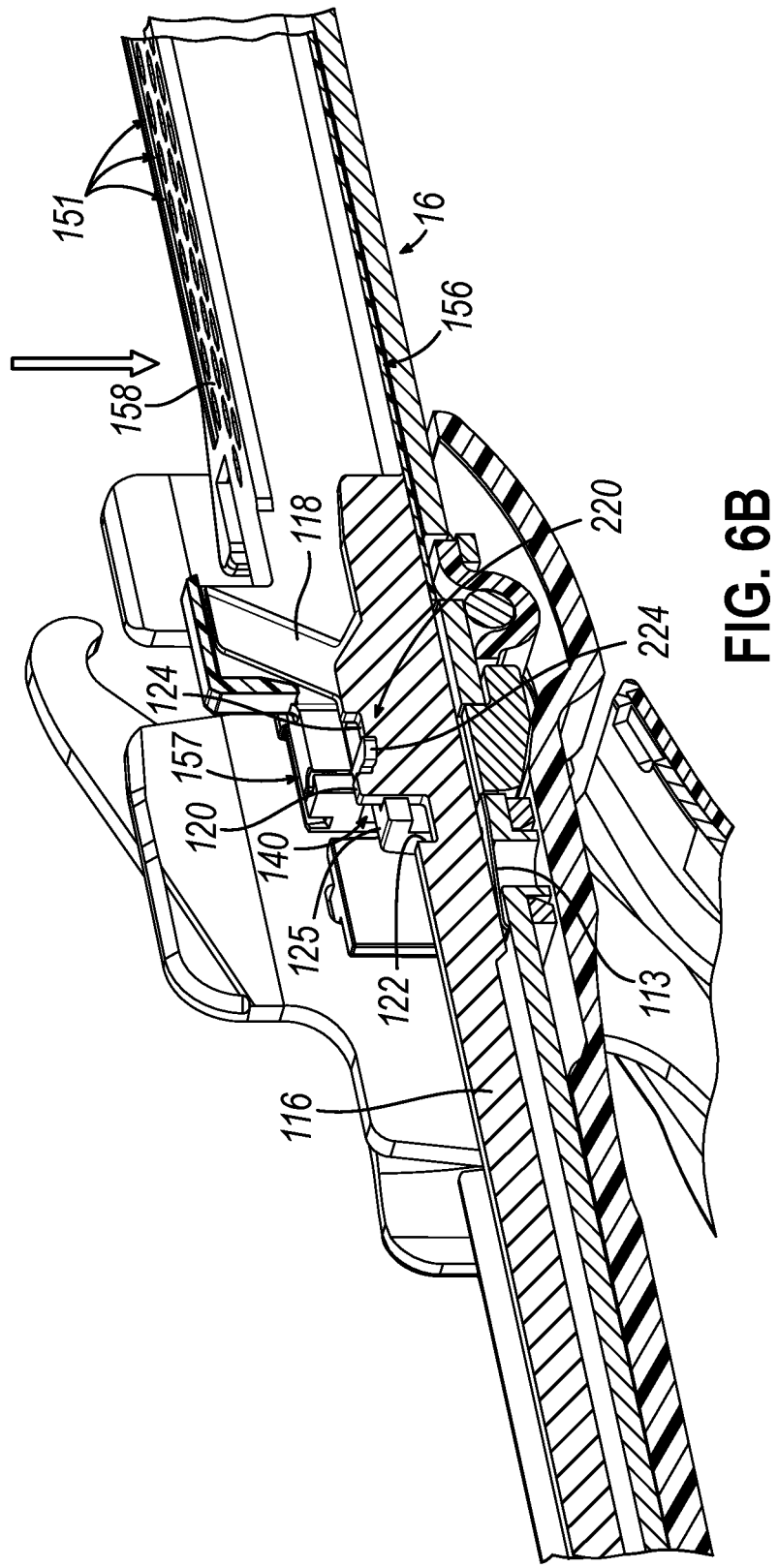
FIG. 6B depicts a sectional perspective view of the staple cartridge assembly of FIG. 4 coupled with the cartridge half of FIG. 1, taken along line 4-4 of FIG. 2, where the firing assembly of FIG. 3 is in an unlocked configuration.
Figure 7A:
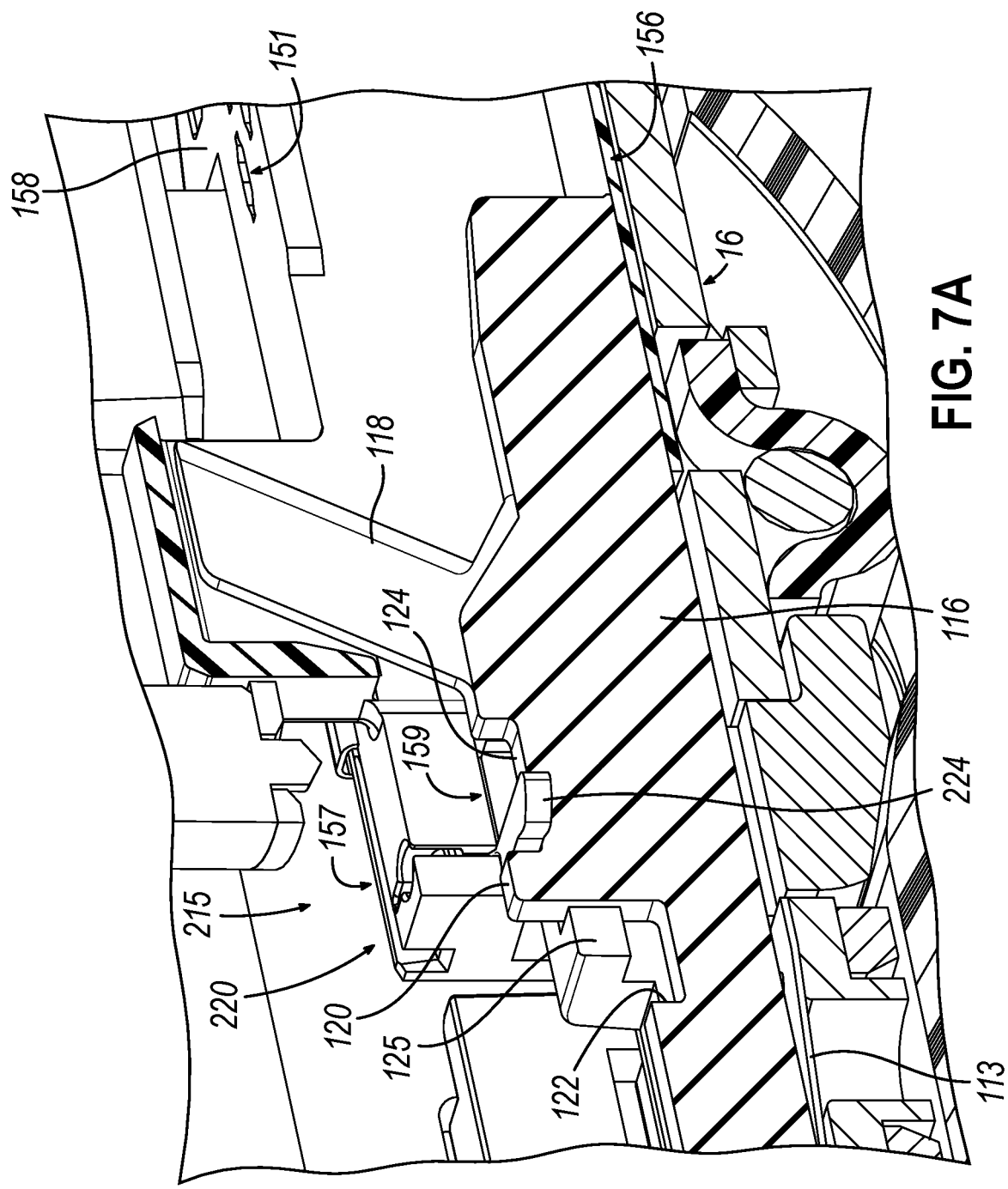
FIG. 7A depicts a sectional perspective view of the cartridge half and the anvil half of FIG. 1 in the fully closed position, taken along line 4-4 of FIG. 2, where the firing assembly of FIG. 3 is in an unlocked configuration and a pre-fired position.

Lockout swing gate (220) is configured to engage knife member (116) to force lockout projection (122) out of engagement with lockout block (125), and into an unlocked configuration, when staple cartridge assembly (150) is suitably loaded into cartridge channel (16) and knife member (116) is in the pre-fired proximal position (as seen in FIGS. 6B and 7A). Additionally, as will be described in greater detail below, lockout swing gate (220) is also configured to pivot out of engagement with actuating knife member (116) during actuation of firing assembly (100) such that lockout swing gate (220) is prevented from further engaging knife member (116) after firing assembly (100) is actuated distally in accordance with the description above.

Figure 7C:
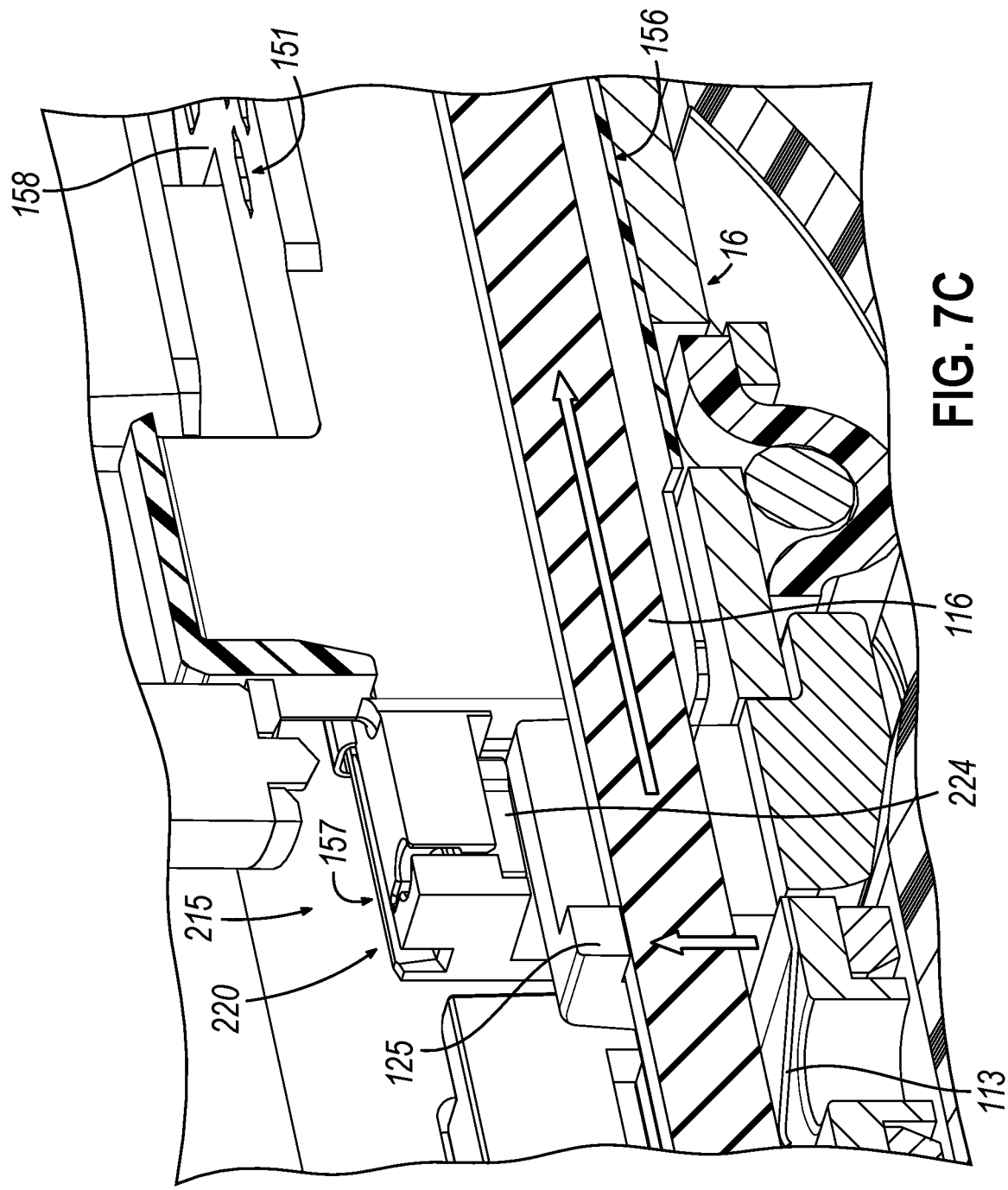
FIG. 7C depicts a sectional perspective view of the cartridge half and the anvil half of FIG. 1 in the fully closed position, taken along line 4-4 of FIG. 2, where the firing assembly of FIG. 3 is in an unlocked configuration and a fired position.
Figure 7D:
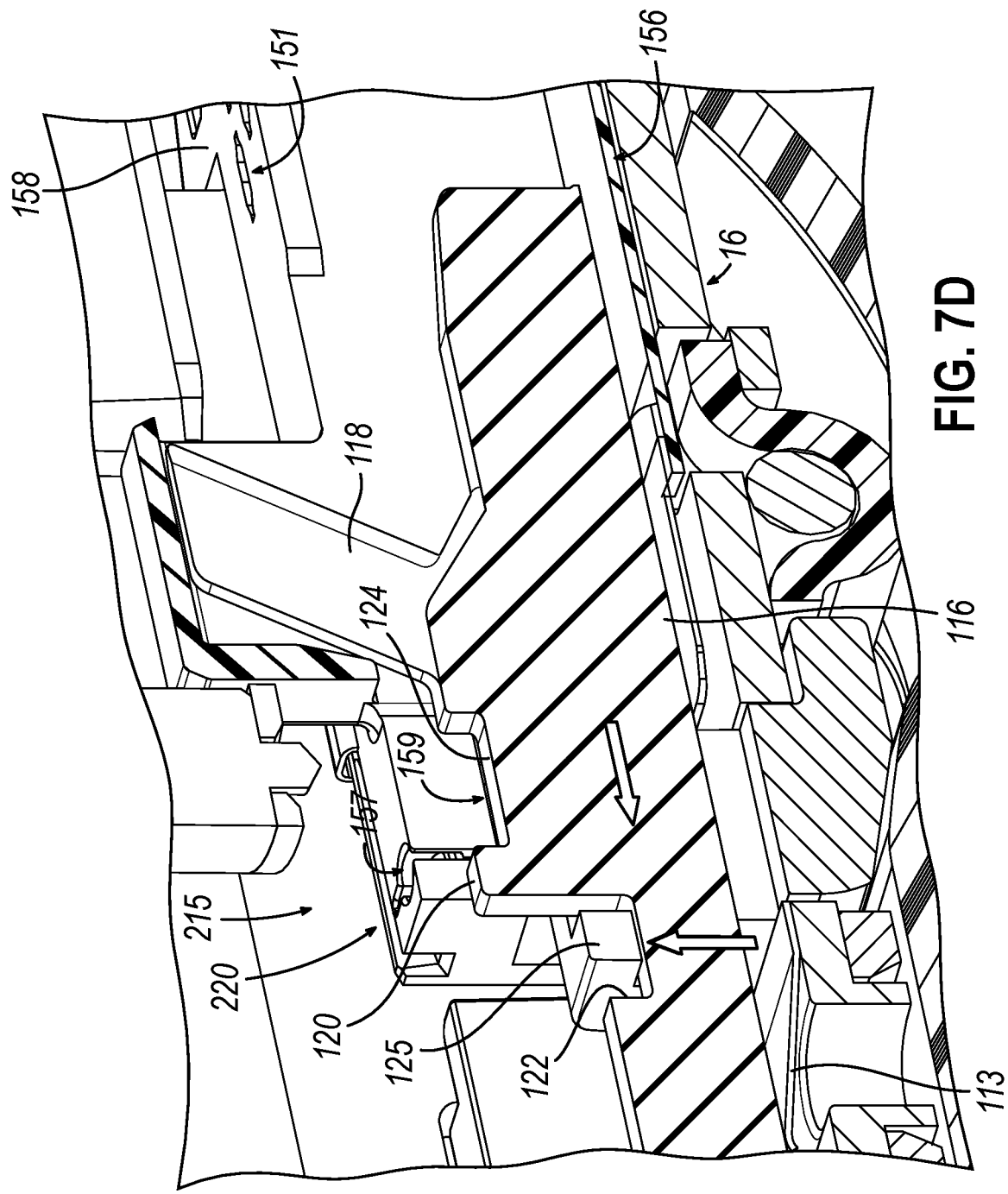
FIG. 7D depicts a sectional perspective view of the cartridge half and the anvil half of FIG. 1 in the fully closed position, taken along line 4-4 of FIG. 2, where the firing assembly of FIG. 3 is in a locked configuration and a post-fired position.

As best shown in FIGS. 4-5, staple cartridge assembly (150) defines both a pivot bore (157) and a sweep away recess (159). Additionally, lockout swing gate (220) includes a pivot post (222) and a leg (224). Pivot post (222) is rotationally housed within pivot bore (157). Leg (224) is configured to rotate from a first position (as shown in FIGS. 4, and 6A-7A) toward a second, disengaged, position (as shown in FIGS. 7B-7D) in response to suitable actuation of firing assembly (100). Leg (224) extends across slot (156) in the first position. Additionally, leg (224) is configured to urge knife member (116) into the unlocked configuration while in the first position. In the second position, leg (224) is housed within sweep away recess (159) such that leg (224) does not extend across slot (156), thereby preventing leg (424) from engaging knife member (116) while in the second position FIGS. 6A-6B show an exemplary loading of staple cartridge assembly (150) into cartridge channel (16). FIG. 6A shows staple cartridge assembly (150) aligned with staple cartridge channel (16) in preparation of loading. At this point, knife member (116) is in the pre-fired proximal position such that actuators (104, 106) are in the position shown in FIG. 1. Leaf spring (113) biases knife member (116) into the locked configuration. In other words, leaf spring (113) biases knife member (116) away from such that lockout block (125) rests within a cutout of knife member (116) partially defined by lockout projection (122). At this point, if an operator attempts to actuate firing assembly (100) from the pre-fired proximal position to a fired position in accordance with the description above, distally presented lockout projection (122) would abut against lockout block (125), thereby preventing distal translation of knife member (116).

Next, as shown in FIG. 6B, an operator may suitably load staple cartridge assembly (150) into cartridge channel (16). At this point, leg (224) of lockout swing gate (220) is in the first position such that leg (224) abuts against a platform (124) of knife member (116) in order to overcome the biasing force of leaf spring (113) and knife member (116) from the locked configuration toward the unlocked configuration. At this moment, an operator may suitably couple cartridge half (12) and anvil half (14) and pivot staple deck (158) and anvil plate (72) toward each other from the open position to the fully closed position in accordance with the description herein.

FIGS. 7A-7B show lockout assembly (215) during an exemplary firing of instrument (100) in accordance with the description above. FIG. 7A shows staple cartridge assembly (150) suitably loaded into cartridge channel (16) as described above, with cartridge half (12) and anvil half (14) in the fully closed position and firing assembly (100) in the pre-fired proximal position. Therefore, at this point, knife member (116) is urged into the unlocked configuration by leg (224) of lockout swing gate (220) such that lockout block (125) will not prevent distal translation of knife member (116). Next an operator may pivot and translate actuator (104, 160) in order to actuate firing assembly in accordance with the description above.

As seen in FIG. 7B, distal actuation of firing assembly (100) causes a sweep away projection (120) of knife member (16) to drive rotation of leg (224) of lockout swing gate (220) from the first position to the second position within sweep away recess (159) of cartridge body (152). Because leg (224) of lockout swing gate (220) no longer extends across slot (156) to abut against platform (124), leaf spring (113) may bias knife member (116) upward. However, it should be understood that lockout projection (122) of knife member (116) has already translated distally past lockout block (125) such that lockout block (125) may not prevent distal translation of knife member (116) at this moment. Next, as seen in FIG. 7C, an operator may further translate knife member (116) within staple cartridge assembly (150) in accordance with the description above to staple and sever tissue captured between anvil plate (72) and staple deck (158).

As shown in FIG. 7D, when an operator proximally translates knife member (116) toward a post-fired proximal position, leg (224) of lockout swing gate (220) is still in the second position housed within sweep away recess (159) of cartridge body (152). Because leg (224) does not span across slot (156) in the second position, leg (224) may no longer contact platform (124) of knife member (116) when coupled with cartridge channel (16). Therefore, leaf spring (113) may urge knife member (116) into the locked configuration, even though staple cartridge assembly (150) is still loaded into cartridge channel (16), thereby preventing a second firing of instrument (10) with the same staple cartridge assembly (150). If an operator desires to use instrument (10) again, an operator may remove the used staple cartridge assembly (150), replace it with a new staple cartridge assembly (150), and repeat the process in accordance with the description above.

II. Exemplary Linear Surgical Stapler Having Alternative Lockout Assembly

As mentioned above, lockout assembly (215) includes a swing gate (220) having a leg (224) that, in a first position (see FIG. 7A), may drive knife member (116) out of engagement with a lockout block (125) such that an operator may fire cartridge assembly (150) in accordance with the description herein. As also mentioned above, swing gate (220) may be driven into a second position (see FIG. 7D) such that after suitably firing staple cartridge assembly (150) in accordance with the description herein, a leaf spring (113) biases knife member (116) into engagement with lockout block (125), thereby preventing a second firing of staple cartridge assembly (150).

Figure 8A:
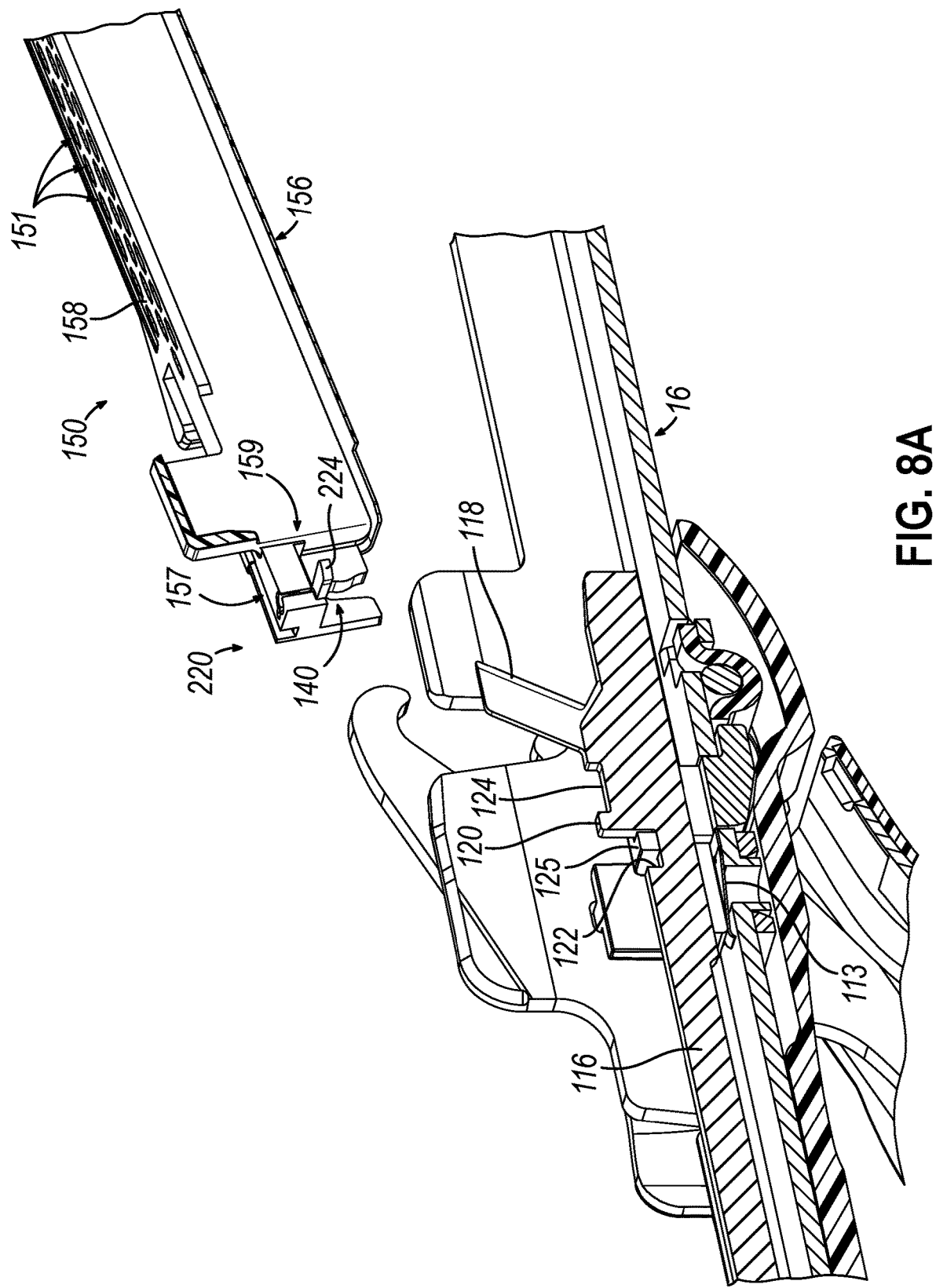
FIG. 8A depicts a sectional perspective view of the staple cartridge assembly of FIG. 4 improperly aligned for coupling with the cartridge half of FIG. 1, taken along line 4-4 of FIG. 2, where the firing assembly of FIG. 3 is in a locked-out configuration.
Figure 8B:
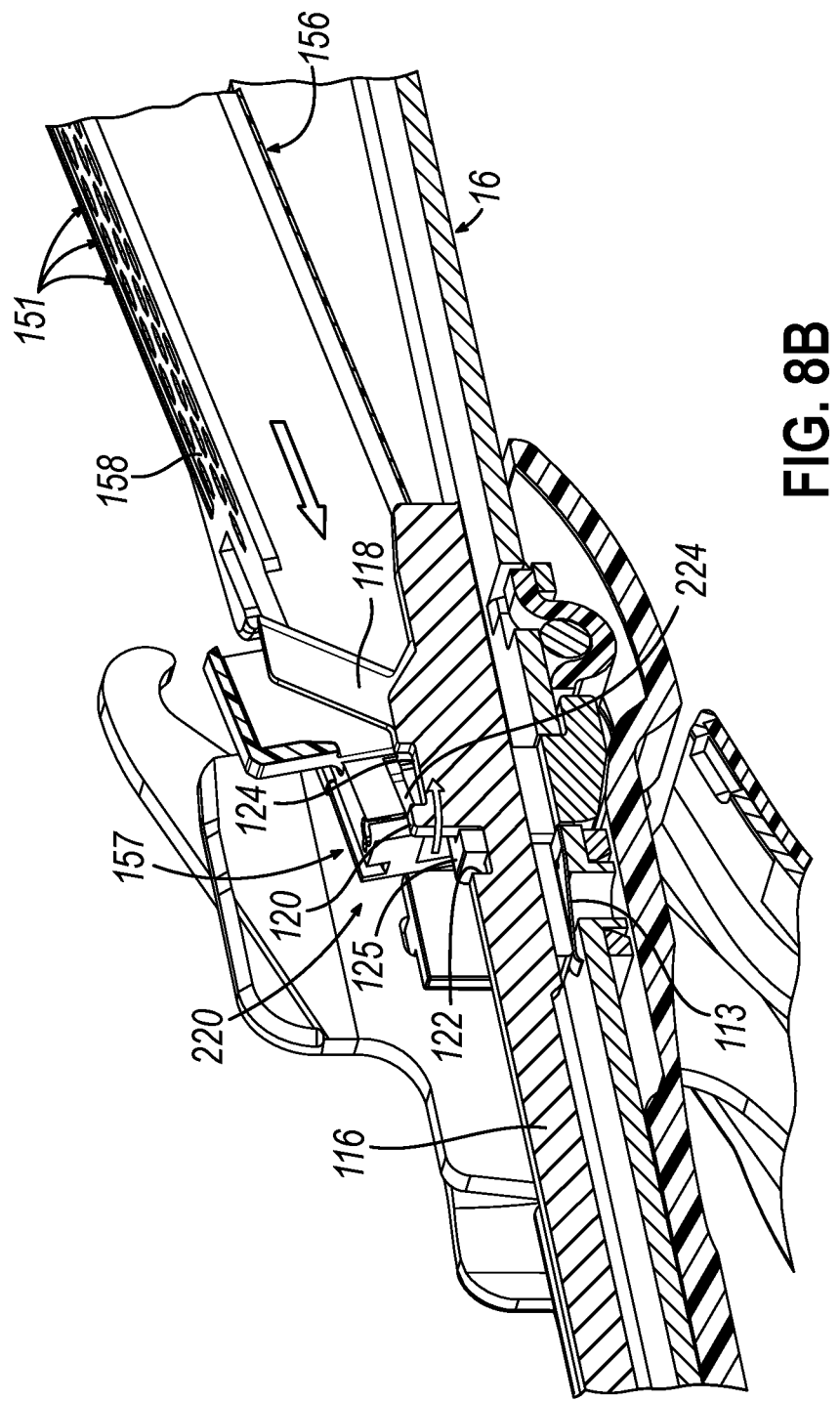
FIG. 8B depicts a sectional perspective view of the staple cartridge assembly of FIG. 4 initially being coupled with the cartridge half of FIG. 1 while improperly aligned with each other, taken along line 4-4 of FIG. 2, where the firing assembly of FIG. 3 is in the locked-out configuration.
Figure 8C:
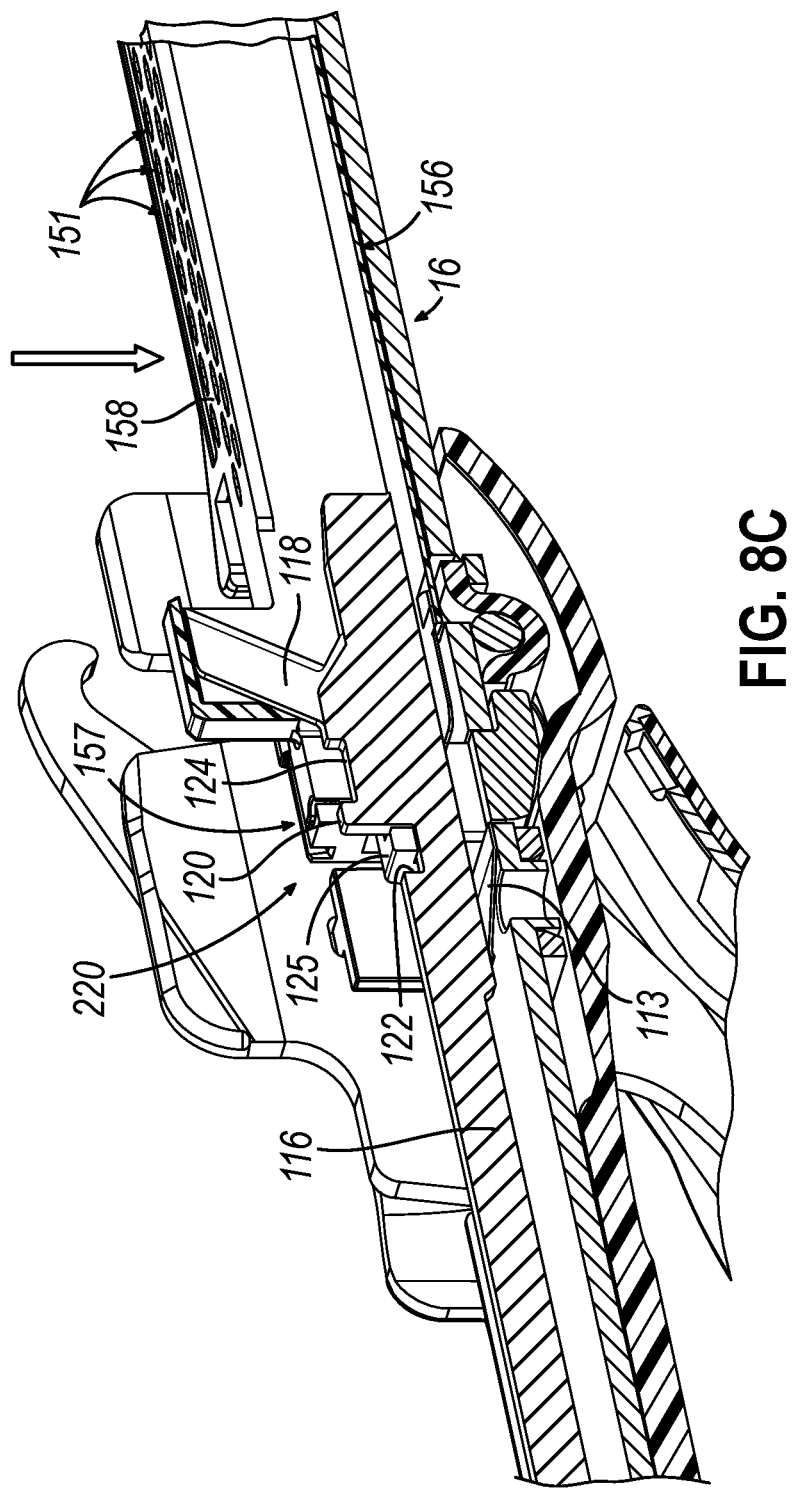
FIG. 8C depicts a sectional perspective view of the staple cartridge assembly of FIG. 4 coupled with the cartridge half of FIG. 1, taken along line 4-4 of FIG. 2, where the firing assembly of FIG. 3 remains in the locked-out configuration.

In some instances, as shown in FIG. 8A, cartridge assembly (150) may be loaded into cartridge channel (16) at an undesirable angle such that a distal tip of cartridge assembly (150) points upward away from cartridge channel (16) while a proximal end of cartridge assembly (150) points downward toward cartridge channel (16). As shown in FIG. 8B, if cartridge assembly (150) is loaded into cartridge channel (16) at such an undesirable angle, knife member (116) may enter into central slot (156) such that the face of leg (224) intended to contact sweep away projection (120) during firing of knife member (116) may make undesirable contact with platform (124), sweep away projection (120), and/or another undesirable component of knife member (116). As shown in FIG. 8C, if contact between the face of leg (224) intended to contact sweep away projection (120) (which thereby rotates swing gate (220) in the second position) makes sufficient undesirable contact with platform (124) and/or sweep away projection (120) during initial insertion of cartridge assembly (150) into cartridge channel (16), swing gate (220) may undesirably rotate into the second position prematurely, prior to firing staple cartridge assembly (150). If swing gate (220) is rotated into the second position prior to firing staple cartridge assembly (150), knife member (116) may be biased into the locked position prior to firing instrument (10) with staple cartridge assembly (150). Therefore, if an operator attempted to fire staple cartridge assembly (150) for a first time in accordance with the description herein, premature engagement between lockout block (125) and lockout projection (122) may prevent such firing.

Therefore, it may be desirable to provide a feature that prevents undesirable contact between platform (124) of knife member (116) (or any other undesirable component) and swing gate (220) during initial coupling of staple cartridge assembly (150) such that even if an operator loaded unspent staple cartridge assembly (150) at an undesirable angle, swing gate (220) may be shielded from undesirable contact that would accidentally and prematurely rotate swing gate (220) into the second position prior to actually firing instrument (10) (which would thereby render an unused staple cartridge assembly (150) incapable of being fired).

Figure 9:
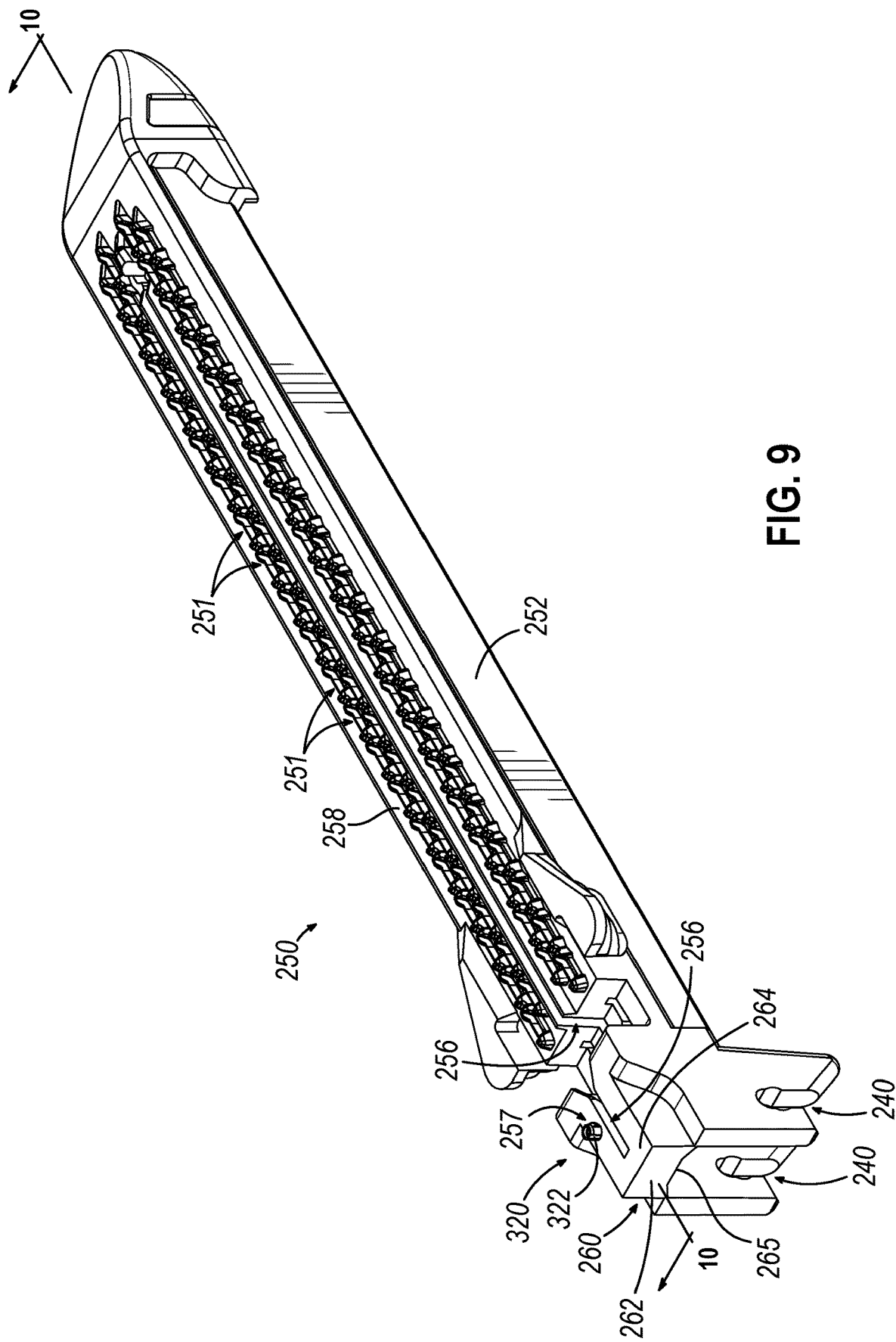
FIG. 9 depicts a perspective view of an alternative staple cartridge assembly.

FIG. 9 shows an exemplary staple cartridge assembly (250) that may be used with and readily incorporated into instrument (10) in replacement of staple cartridge assembly (150) described above. Therefore, staple cartridge assembly (250) may be substantially similar to staple cartridge assembly (150) described above, with differences elaborated below. In particular, staple cartridge assembly (160) includes a proximal end having laterally extending bridge member (260) that helps define a terminating proximal end of a central slot (256) defined by a cartridge body (252). As will be described in greater detail below, laterally extending bridge member (260) is configured shield a swing gate (320) from contact with platform (124) of knife member (116) (or any other undesirable component) during initial coupling of staple cartridge assembly (250) if staple cartridge assembly (250) is accidentally inserted into cartridge channel (16) at an undesirable angle (similar to the angle formed by staple cartridge assembly (150) shown in FIGS. 8A-8B). Therefore, bridge member (260) may help prevent swing gate (320) from inadvertently and prematurely moving into the second position during initial coupling of staple cartridge assembly (250) if staple cartridge assembly (250) is inserted at an angle where the proximal end of cartridge assembly (250) faces downward toward cartridge channel (16) while the distal end of cartridge assembly (250) faces away from cartridge channel (16).

Staple cartridge assembly (250) includes a cartridge body (252), coupling cutouts (240), a staple deck (258), a plurality of staple openings (251), a central slot (256), a pivot bore (257), and a sweep away recess (259); which may be substantially similar to cartridge body (152), coupling cutouts (140), staple deck (158), staple openings (151), central slot (156), pivot bore (157), and sweep away recess (159) described above, with differences elaborated below. Therefore, staple cartridge assembly (250) may be readily coupled to elongate cartridge channel (16) such that firing assembly (100) may actuate within staple cartridge assembly (250) in order to simultaneously staple and sever tissue grasped between anvil plate (72) and staple deck (258) in accordance with the description herein.

Figure 10:
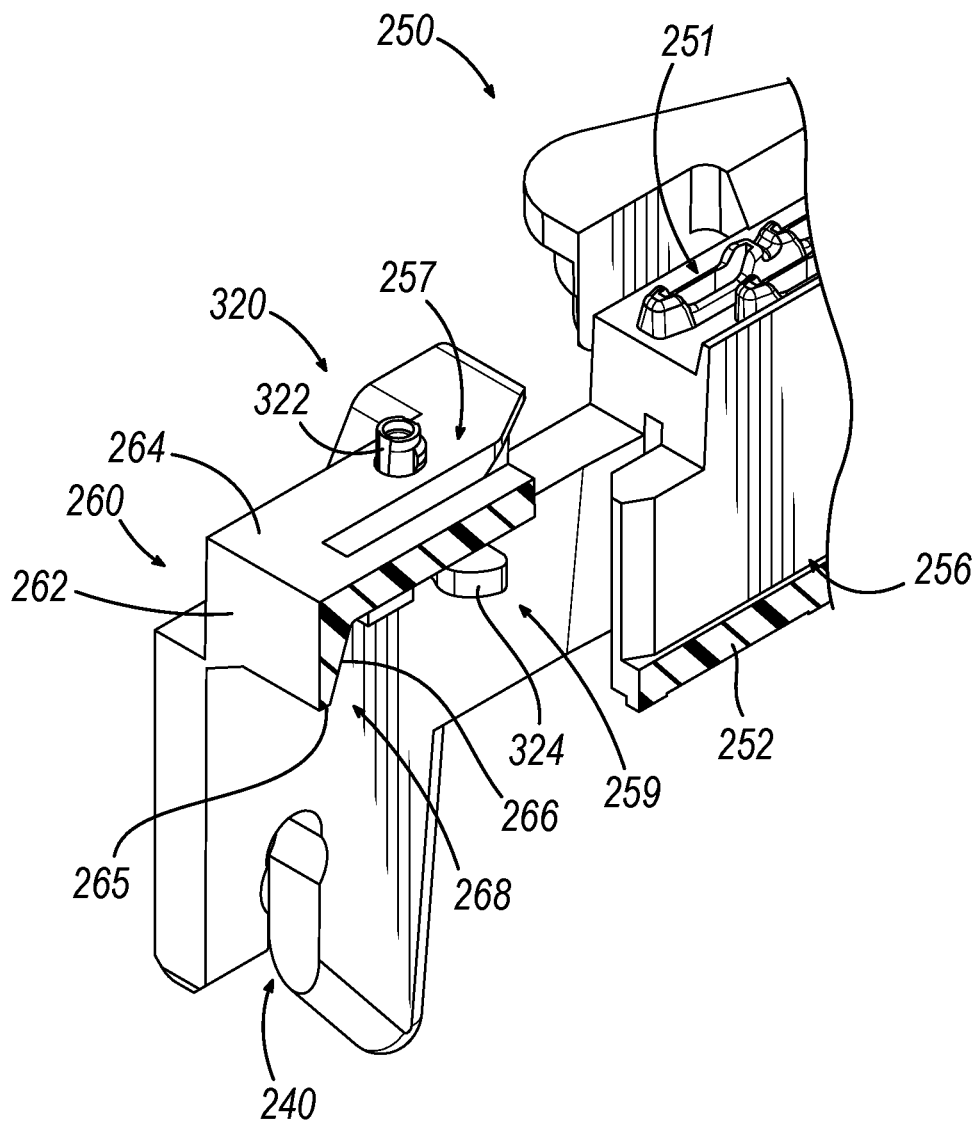
FIG. 10 depicts a sectional perspective view of a proximal end of the staple cartridge assembly of FIG. 9, taken along line 10-10 of FIG. 9.

As best shown in FIG. 10, a proximal end of cartridge body (252) houses a swing gate (320). Swing gate (320) may be substantially similar to swing gate (220) described above. Therefore, swing gate (320) includes a pivot post (322) and a leg (324); which are substantially similar to pivot post (222) and leg (224) described above. Swing gate (320), lockout block (125), and leaf spring (113) together form a lockout assembly (315) that is substantially similar to lockout assembly (215) described above. Therefore, swing gate (320), while in the first position, is configured to drive knife member (116) out of engagement with lockout block (125) when initially coupled with cartridge channel (16) such that knife member (116) may be distally actuated in order to fire staples out of staple cartridge (250). Additionally, sweep away projection (120) is configured to drive swing gate (320) into a second position within sweep away recess (259) such that once knife member (116) is actuated proximally into a post-fired position, leaf spring (113) may bias knife member (116) into a locked-out configuration to prevent knife member (116) from being actuated distally within the same cartridge body (252) a second time.

Unlike cartridge body (152) described above, which defines a central slot (159) extending through a proximal end of body (152), cartridge body (252) includes laterally extending bridge member (260), which extends across a proximal end of cartridge body (252) such that central slot (259) is closed off. In other words, central slot (259) does not extend all the way through a proximal end of cartridge body (252). Therefore, knife member (116) may not enter central slot (259) via the proximal end of cartridge body (252). Instead, life member (116) may initially enter central slot (259) via the underside of cartridge body (252).

Laterally extending bridge member (260) of the current example includes a proximally facing surface (262), an upward facing surface (264), a bottom edge (265), and an inward facing surface (266). Proximally facing surface (262) extends between bottom edge (265) and upward facing surface (264). Interior facing surface (266) helps partially define an internal cavity (268) that may receive selected portions of knife member (116) once cartridge assembly (250) is suitably coupled to cartridge channel (16). Laterally extending bridge member (260) acts as a guard for swing gate (320) to prevent accidental rotation of leg (324) into sweep away recess (259) prior to staple cartridge assembly (250) being used in accordance with the description herein. Any one or more of surfaces (262, 264, 266) or edge (265) may act as shield if cartridge body (252) is inserted at an angle where a distal end of cartridge body (252) is pointed upward away from channel (16) and a proximal end of cartridge body (252) is pointed downward toward channel (16).

Figure 11A:
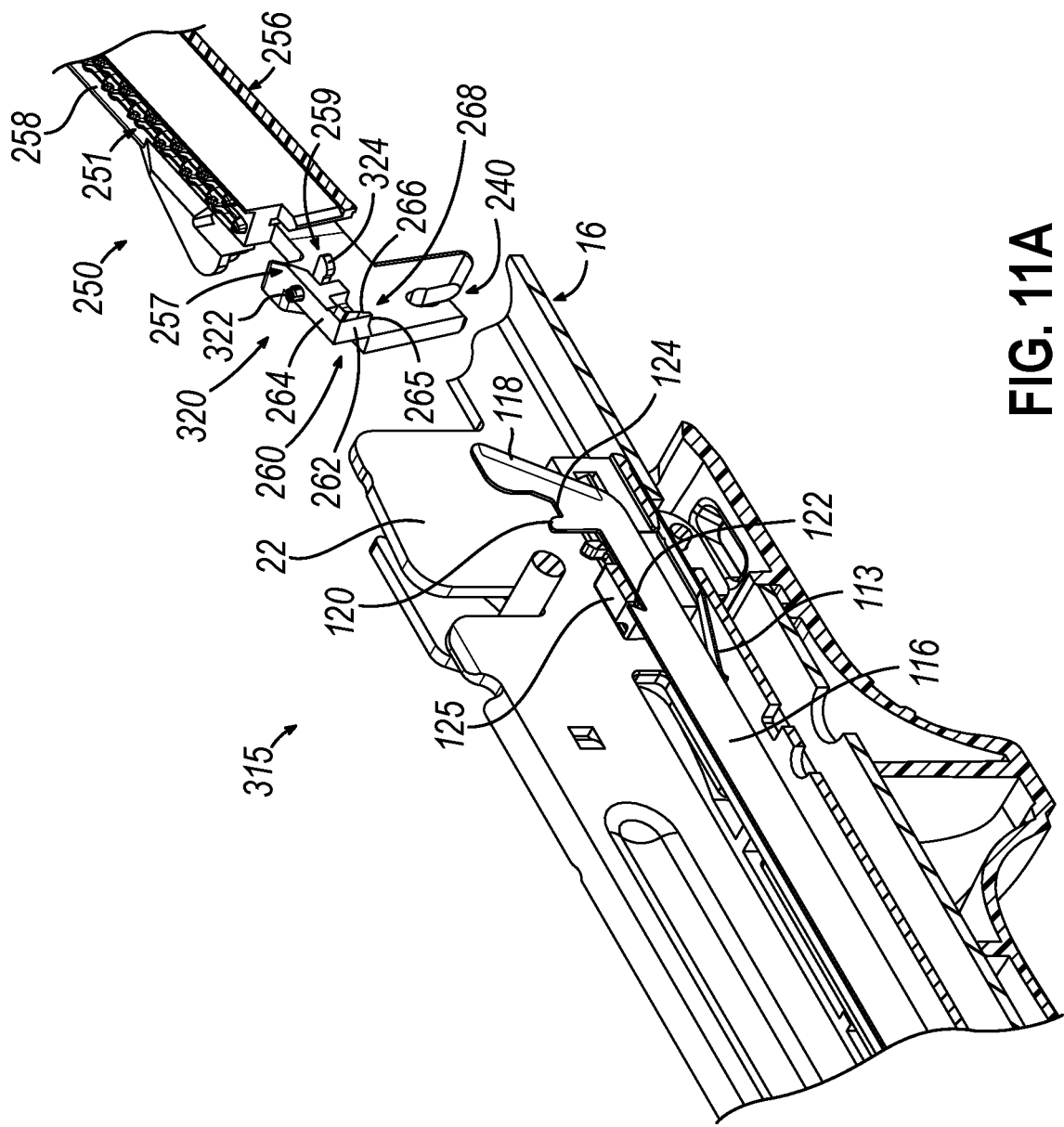
FIG. 11A depicts a sectional perspective view of the staple cartridge assembly of FIG. 9 improperly aligned for coupling with the cartridge half of FIG. 1, where the firing assembly of FIG. 3 is in a locked-out configuration, taken along line 10-10 of FIG. 9.
Figure 11B:
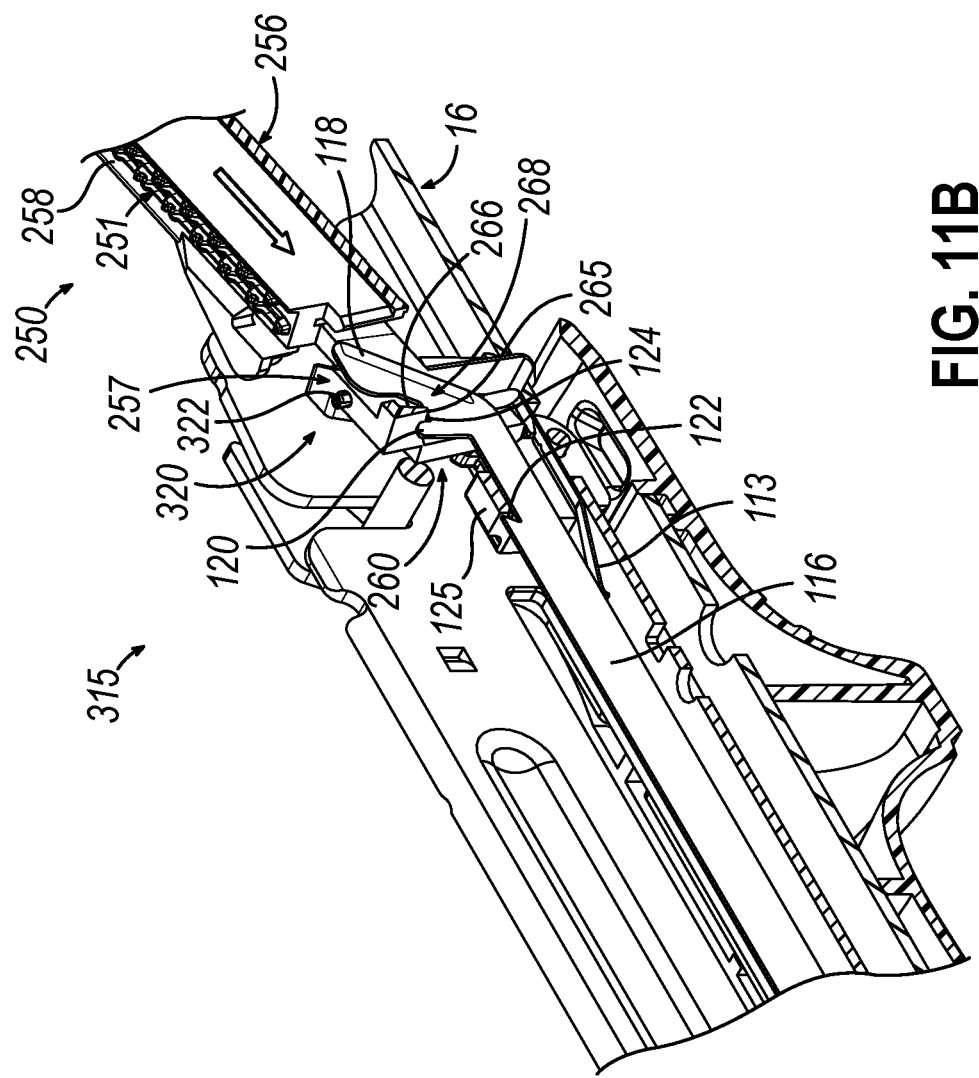
FIG. 11B depicts a sectional perspective view of the staple cartridge assembly of FIG. 9 initially being coupled with the cartridge half of FIG. 1 while improperly aligned with each other, where the firing assembly of FIG. 3 is in a locked-out configuration, taken along line 10-10 of FIG. 9.
Figure 11C:
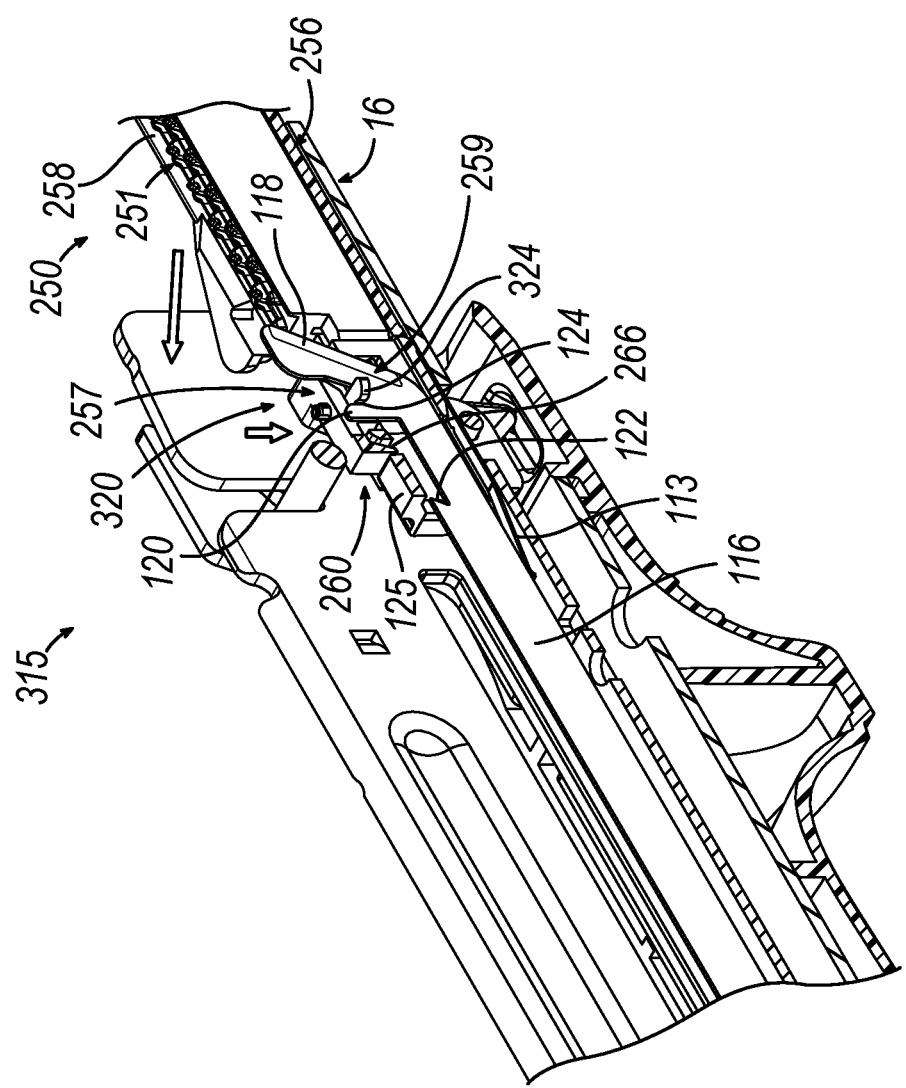
FIG. 11C depicts a sectional perspective view of the staple cartridge assembly of FIG. 9 coupled with the cartridge half of FIG. 1, where the firing assembly of FIG. 3 is in an unlocked configuration, taken along line 10-10 of FIG. 9.

FIGS. 11A-11C show an exemplary coupling of staple cartridge assembly (250) and cartridge channel (16). In particular, FIGS. 11A-11C show an exemplary insertion of staple cartridge assembly (250) at an undesirable angle, where bridge member (260) prevents accidental and premature rotation of leg (342) into sweep away recess (259). As shown in FIG. 11A, in some instances an operator may accidentally try to couple staple cartridge assembly (250) with cartridge channel (16) while a proximal end of cartridge body (252) is positioned closer to channel (16) as compared to a distal end of the cartridge body (252), similar to that shown in FIG. 8A. Therefore, if an operator further inserts cartridge body (252) into cartridge channel (16), as shown in FIG. 11B, surfaces (262, 264, 266) and/or edge (265) may contact platform (124) and/or sweep away projection (120), thereby preventing platform (124) or sweep away projection (120) from entering central slot (259) via a proximal end of cartridge body (252) and accidentally driving leg (324) into sweep away recess (259). In some instances, contact between bridge member (260) and knife member (116) may be sufficient to temporarily drive knife member (116) into an unlocked position during initial insertion of staple cartridge assembly (250).

Figure 12:
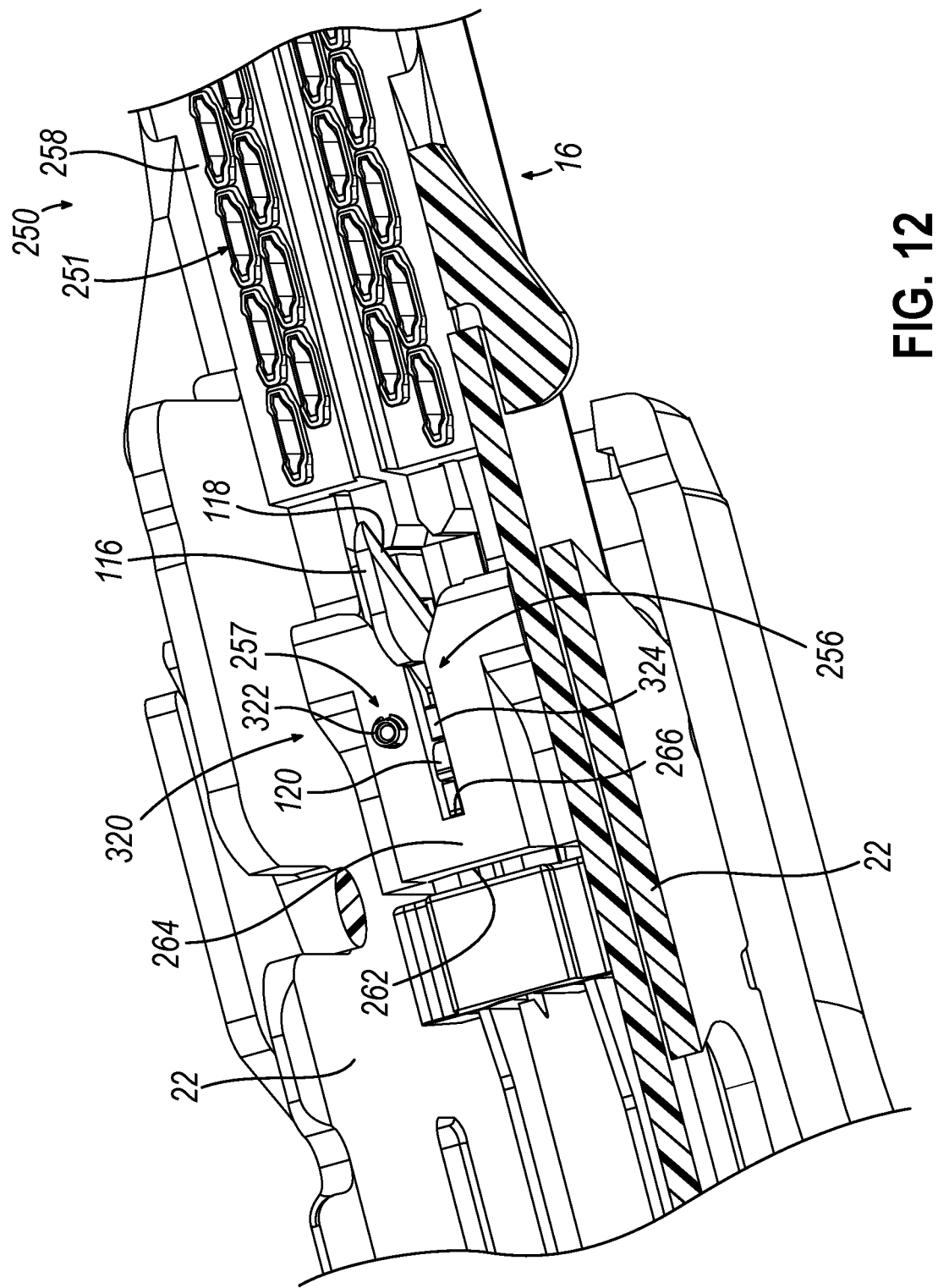
FIG. 12 depicts a perspective view of the staple cartridge assembly of FIG. 9 coupled with the cartridge half of FIG. 1.

Once staple cartridge assembly (250) is advanced a suitable proximal distance into cartridge channel (16), an operator may then rotate a proximal end of staple cartridge assembly (250) downward to suitably couple with cartridge channel (16) as shown in FIG. 11C and FIG. 12. It should be understood that even though a user accidentally inserted staple cartridge assembly (250) in an angular orientation that could have previously driven leg (224) of staple cartridge assembly (150) into sweep away recess (159), bridge member (260) prevented leg (324) from being accidentally driven into sweep away recess (259), thereby still allowing staple cartridge assembly (250) to be used in accordance with the description herein.

While in the current example bridge member (260) includes proximally facing surface (262), upwardly facing surface (264), edge (265), and interior surface (266); it should be understood that bridge member (260) may include any suitable geometry that would be apparent to one skilled in the art in view of the teachings herein. For example, bridge member (260) may include a rod structure that extends laterally across central slot (256).

III. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

EXAMPLE 1

A surgical stapler comprising: (a) a first half comprising a first elongate member, and a surface configured to form staples; (b) a second half configured to releasably couple with the first half, wherein the second half comprises a second elongate member having a distal cartridge channel; (c) a staple cartridge assembly configured to selectively couple with the distal cartridge channel of the second elongate member, wherein the staple cartridge assembly comprises a cartridge body defining a central slot; (d) a firing assembly comprising a firing beam configured to actuate within the central slot of the staple cartridge assembly, wherein the firing assembly is configured to actuate from a pre-fired proximal position toward a distal position in order to staple and sever tissue captured between the surface of the first half and the staple cartridge assembly; (e) a lockout assembly configured to prevent distal translation of the firing assembly in a locked configuration and allow distal translation of the firing assembly in an unlocked configuration, wherein the lockout assembly comprises a body associated with the staple cartridge assembly and configured to transition between a first position and a second position, wherein the body is configured to drive the firing assembly into the unlocked configuration while in the first position, wherein the body is configured to permit the firing assembly to assume the locked configuration while the body is in the second position, wherein the firing beam is configured to drive the body from the first position into the second in response to actuating from the pre-fired proximal position toward the distal position; and (f) a bridge member located at a proximal end of the central slot and extending across the central slot, wherein the bridge member is configured to inhibit the firing beam from entering the central slot via the proximal end of the central slot as the staple cartridge assembly is selectively coupled with the distal cartridge channel.

EXAMPLE 2

The surgical stapler of any one or more of the preceding Examples, further comprising a latching member operable to selectively clamp the first half against the second half to thereby define a clamped state of the surgical stapler.

EXAMPLE 3

The surgical stapler of any one or more of the preceding Examples, wherein the body of the lockout assembly comprises a swing gate rotatably coupled with the staple cartridge assembly.

EXAMPLE 4

The surgical stapler of any one or more of the preceding Examples, wherein the swing gate further comprises a pivot post and a leg, wherein the leg extends across the channel in the first position.

EXAMPLE 5

The surgical stapler of any one or more of the preceding Examples, wherein the staple cartridge assembly defines a pivot bore, wherein the pivot post is rotatably disposed within the pivot bore.

EXAMPLE 6

The surgical stapler of any one or more of the preceding Examples, wherein the staple cartridge assembly defines a sweep away recess dimensioned to house the leg in the second position.

EXAMPLE 7

The surgical stapler of any one or more of the preceding Examples, wherein the bridge member is located above a portion of the firing beam that is directly adjacent to the bridge member.

EXAMPLE 8

The surgical stapler of any one or more of the preceding Examples, wherein the firing beam comprising a distal knife member, wherein the distal knife member extends distally past the bridge member when the staple cartridge assembly is coupled with the distal cartridge channel.

EXAMPLE 9

The surgical stapler of any one or more of the preceding Examples, wherein the lockout assembly comprises a bias spring configured to bias the firing beam into the locking configuration.

EXAMPLE 10

The surgical stapler of any one or more of the preceding Examples, wherein the bias spring comprises a leaf spring.

EXAMPLE 11

The surgical stapler of any one or more of the preceding Examples, wherein the lockout assembly comprises a lockout body configured to engage the firing beam in the locked configuration while the firing assembly is in the pre-fired proximal position

EXAMPLE 12

The surgical stapler of any one or more of the preceding Examples, wherein the firing assembly comprises a first actuator and a second actuator.

EXAMPLE 13

The surgical stapler of any one or more of the preceding Examples, where the first actuator is located on a first side of the second half, wherein the second actuator is located on a second side of the second half

EXAMPLE 14

The surgical stapler of any one or more of the preceding Examples, wherein the firing assembly comprises a cam member configured to drive a plurality of staples out of the staple cartridge.

EXAMPLE 15

The surgical stapler of any one or more of the preceding Examples, wherein the cam member is fixed relative to the firing beam.

EXAMPLE 16

A surgical stapler comprising: (a) a first half comprising a first elongate member, and a surface configured to form staples; (b) a second half configured to releasably couple with the first half, wherein the second half comprises a second elongate member having a distal cartridge channel; (c) a staple cartridge assembly configured to selectively couple with the distal cartridge channel of the second elongate member, wherein the staple cartridge assembly comprises a cartridge body defining a central slot; (d) a firing assembly comprising a firing beam configured to actuate within the central slot of the staple cartridge assembly, wherein the firing assembly is configured to actuate from a pre-fired proximal position toward a distal position in order to staple and sever tissue captured between the surface of the first half and the staple cartridge assembly; (e) a lockout assembly configured to prevent firing of the firing assembly in a locked configuration and allow firing of the firing assembly in an unlocked configuration, wherein the lockout assembly comprises a swing gate pivotally coupled with the staple cartridge assembly and configured to extend across the central slot in a first position and extend along one side of the central slot in a second position, wherein the swing gate is configured to drive the firing assembly into the unlocked configuration while in the first position, wherein the swing gate is configured to permit the firing assembly to assume the locked configuration while the swing gate is in the second position, wherein the firing beam is configured to drive the swing gate from the first position into the second position in response to actuating from the pre-fired proximal position toward the distal position; and (f) a bridge member located proximal to the swing gate and extending across the central slot, wherein the bridge member is configured to inhibit the firing beam from driving the swing gate into the second position as the staple cartridge assembly is inserted into the distal cartridge channel.

EXAMPLE 17

The surgical stapler of any one or more of the preceding Examples, wherein the bridge member is located at a proximal end of the staple cartridge assembly.

EXAMPLE 18

The surgical stapler of any one or more of the preceding Examples, wherein the bridge member comprises a downwardly facing edge configured to contact the firing beam as the bridge member inhibits the firing beam from driving the swing gate into the second position as the staple cartridge assembly is inserted into the distal cartridge.

EXAMPLE 19

The surgical stapler of any one or more of the preceding Examples, wherein the bridge member defines an internal cavity.

EXAMPLE 20

A staple cartridge assembly configured to couple with a cartridge channel of a surgical stapler, the staple cartridge assembly comprising: (a) a staple cartridge body defining a central slot dimensioned to slidably receive a firing beam of the surgical stapler, comprising: (i) a proximal end, (ii) a distal end, and (iii) a staple deck extending between the proximal end and the distal end, wherein the staple deck defines a plurality of staple openings; (b) a swing gate pivotably coupled with the staple cartridge body, wherein the swing gate is configured to pivot between a first position and a second position, wherein the swing gate extends across the central slot in the first position, wherein the swing gate extends alongside the central slot in the second position; and (c) a bridge member extending across the central slot and located proximally relative to the swing gate, wherein the bridge member defines a closed proximal end of the central slot.

IV. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Further, any one or more of the teachings, expressions, embodiments, examples, etc. described herein may be combined with any one or more of the teachings, expressions, embodiments, examples, etc. described in U.S. Pat. No. 10,631,866, entitled "Release Mechanism for Linear Surgical Stapler," issued on Apr. 28, 2020; U.S. Pat. No. 10,667,818, entitled "Lockout Assembly for Linear Surgical Stapler," issued on Jun. 2, 2020; U.S. Pat. No. 10,932,781, entitled "Features to Align and Close Linear Surgical Stapler", issued on Mar. 2, 2021; U.S. Pat. No. 10,898,197, entitled "Releasable Coupling Features for Proximal Portions of Linear Surgical Stapler," issued on Jan. 26, 2021; U.S. Pat. No. 10,874,398, entitled "Firing Lever Assembly for Linear Surgical Stapler," issued on Dec. 29, 2020; U.S. Pat. No. 10,687,819, entitled "Clamping Mechanism for Linear Surgical Stapler," issued on Jun. 23, 2020; U.S. Pat. No. 10,898,187, entitled "Firing System for Linear Surgical Stapler," issued on Jan. 26, 2021; U.S. Pub. No. 2020/0046353, entitled "Clamping Assembly for Linear Surgical Stapler," published on Feb. 13, 2020; issued as U.S. Pat. No. 11,278,285 on Mar. 22, 2022; U.S. Pat. No. 11,045,193, entitled "Anvil Assembly for Linear Surgical Stapler," issued on Jun. 29, 2021; U.S. Pat. No. 10,905,419, entitled "Closure Assembly for Linear Surgical Stapler," issued on Feb. 2, 2021; and/or U.S. Pat. No. 11,033,266, entitled "Decoupling Mechanism for Linear Surgical Stapler," issued on Jun. 15, 2021. The disclosure of each of these applications is incorporated by reference herein.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, California.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical stapler comprising:
   (a) a first half comprising a first elongate member, and a surface configured to form staples;
   (b) a second half configured to releasably couple with the first half, wherein the second half comprises a second elongate member having a distal cartridge channel;
   (c) a staple cartridge assembly configured to selectively couple with the distal cartridge channel of the second elongate member, wherein the staple cartridge assembly comprises a cartridge body defining a central slot;
   (d) a firing assembly comprising a firing beam configured to actuate within the central slot of the staple cartridge assembly, wherein the firing assembly is configured to actuate from a pre-fired proximal position toward a distal position in order to staple and sever tissue captured between the surface of the first half and the staple cartridge assembly;
   (e) a lockout assembly configured to prevent distal translation of the firing assembly in a locked configuration and allow distal translation of the firing assembly in an unlocked configuration, wherein the lockout assembly comprises a body associated with the staple cartridge assembly and configured to transition between a first position and a second position, wherein the body is configured to drive the firing assembly into the unlocked configuration while in the first position, wherein the body is configured to permit the firing assembly to assume the locked configuration while the body is in the second position, wherein the firing beam is configured to drive the body from the first position into the second in response to actuating from the pre-fired proximal position toward the distal position; and
   (f) a bridge member affixed to the cartridge body and located at a proximal end of the central slot and extending across the central slot, wherein the bridge member is configured to inhibit the firing beam from entering the central slot via the proximal end of the central slot as the staple cartridge assembly is selectively coupled with the distal cartridge channel.

2. The surgical stapler of claim 1, further comprising a latching member operable to selectively clamp the first half against the second half to thereby define a clamped state of the surgical stapler.

3. The surgical stapler of claim 1, wherein the body of the lockout assembly comprises a swing gate rotatably coupled with the staple cartridge assembly.

4. The surgical stapler of claim 3, wherein the swing gate further comprises a pivot post and a leg, wherein the leg extends across the channel in the first position.

5. The surgical stapler of claim 4, wherein the staple cartridge assembly defines a pivot bore, wherein the pivot post is rotatably disposed within the pivot bore.

6. The surgical stapler of claim 5, wherein the staple cartridge assembly defines a sweep away recess dimensioned to house the leg in the second position.

7. The surgical stapler of claim 1, wherein the bridge member is located above a portion of the firing beam that is directly adjacent to the bridge member.

8. The surgical stapler of claim 7, wherein the firing beam comprising a distal knife member, wherein the distal knife member extends distally past the bridge member when the staple cartridge assembly is coupled with the distal cartridge channel.

9. The surgical stapler of claim 1, wherein the lockout assembly comprises a bias spring configured to bias the firing beam into the locking configuration.

10. The surgical stapler of claim 9, wherein the bias spring comprises a leaf spring.

11. The surgical stapler of claim 9, wherein the lockout assembly comprises a lockout body configured to engage the firing beam in the locked configuration while the firing assembly is in the pre-fired proximal position.

12. The surgical stapler of claim 1, wherein the firing assembly comprises a first actuator and a second actuator.

13. The surgical stapler of claim 12, where the first actuator is located on a first side of the second half, wherein the second actuator is located on a second side of the second half.

14. The surgical stapler of claim 1, wherein the firing assembly comprises a cam member configured to drive a plurality of staples out of the staple cartridge.

15. The surgical stapler of claim 1, wherein the cam member is fixed relative to the firing beam.

16. A surgical stapler comprising:
   (a) a first half comprising a first elongate member, and a surface configured to form staples;
   (b) a second half configured to releasably couple with the first half, wherein the second half comprises a second elongate member having a distal cartridge channel;
   (c) a staple cartridge assembly configured to selectively couple with the distal cartridge channel of the second elongate member, wherein the staple cartridge assembly comprises a cartridge body defining a central slot;
   (d) a firing assembly comprising a firing beam configured to actuate within the central slot of the staple cartridge assembly, wherein the firing assembly is configured to actuate from a pre-fired proximal position toward a distal position in order to staple and sever tissue captured between the surface of the first half and the staple cartridge assembly;
   (e) a lockout assembly configured to prevent firing of the firing assembly in a locked configuration and allow firing of the firing assembly in an unlocked configuration, wherein the lockout assembly comprises a swing gate pivotally coupled with the staple cartridge assembly and configured to extend across the central slot in a first position and extend along one side of the central slot in a second position, wherein the swing gate is configured to drive the firing assembly into the unlocked configuration while in the first position, wherein the swing gate is configured to permit the firing assembly to assume the locked configuration while the swing gate is in the second position, wherein the firing beam is configured to drive the swing gate from the first position into the second position in response to actuating from the pre-fired proximal position toward the distal position; and (f) a bridge member integrally connected with the cartridge body, wherein the bridge member is located proximal to the swing gate and extends across the central slot, wherein the bridge member is configured to inhibit the firing beam from driving the swing gate into the second position as the staple cartridge assembly is inserted into the distal cartridge channel.

17. The surgical stapler of claim 16, wherein the bridge member is located at a proximal end of the staple cartridge assembly.

18. The surgical stapler of claim 17, wherein the bridge member comprises a downwardly facing edge configured to contact the firing beam as the bridge member inhibits the firing beam from driving the swing gate into the second position as the staple cartridge assembly is inserted into the distal cartridge.

19. The surgical stapler of claim 18, wherein the bridge member defines an internal cavity.

20. A staple cartridge assembly configured to couple with a cartridge channel of a surgical stapler, the staple cartridge assembly comprising:

(a) a staple cartridge body defining a central slot dimensioned to slidably receive a firing beam of the surgical stapler, comprising:
   (i) a proximal end,
   (ii) a distal end, and
   (iii) a staple deck extending between the proximal end and the distal end, wherein the staple deck defines a plurality of staple openings;

(b) a swing gate pivotably coupled with the staple cartridge body, wherein the swing gate is configured to pivot between a first position and a second position, wherein the swing gate extends across the central slot in the first position, wherein the swing gate extends alongside the central slot in the second position; and (c) a bridge member affixed to the staple cartridge body, wherein the bridge extends across the central slot and is located proximally relative to the swing gate, wherein the bridge member defines a closed proximal end of the central slot.

* * * * *